United States Patent
Sluis-Cremer et al.

(10) Patent No.: US 10,980,811 B2
(45) Date of Patent: Apr. 20, 2021

(54) REVERSAL OF FOSFOMYCIN RESISTANCE

(71) Applicants: University of Pittsburgh—Of the Commonwealth System of Higher Education, Pittsburgh, PA (US); University of Maryland, Baltimore, Baltimore, MD (US)

(72) Inventors: Nicolas Paul Sluis-Cremer, Pittsburgh, PA (US); Adam Daniel Tomich, Pittsburgh, PA (US); Yohei Doi, Pittsburgh, PA (US); Eric J. Sundberg, Baltimore, MD (US); Erik H. Klontz, Baltimore, MD (US); Steven Fletcher, Baltimore, MD (US)

(73) Assignees: University of Pittsburgh—of the Commonwealth System of Higher Education, Pittsburgh, PA (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 16/476,845

(22) PCT Filed: Jan. 11, 2018

(86) PCT No.: PCT/US2018/013282
§ 371 (c)(1),
(2) Date: Jul. 9, 2019

(87) PCT Pub. No.: WO2018/132547
PCT Pub. Date: Jul. 19, 2018

(65) Prior Publication Data
US 2019/0358232 A1 Nov. 28, 2019

Related U.S. Application Data

(60) Provisional application No. 62/445,662, filed on Jan. 12, 2017.

(51) Int. Cl.
| | |
|---|---|
| *A61K 31/519* | (2006.01) |
| *A61P 31/04* | (2006.01) |
| *A61K 31/665* | (2006.01) |
| *C07D 487/04* | (2006.01) |
| *C07D 519/00* | (2006.01) |

(52) U.S. Cl.
CPC .......... *A61K 31/519* (2013.01); *A61K 31/665* (2013.01); *A61P 31/04* (2018.01); *C07D 487/04* (2013.01); *C07D 519/00* (2013.01)

(58) Field of Classification Search
CPC .. C07D 487/04; C07D 519/00; A61K 31/519; A61P 31/04
See application file for complete search history.

(56) References Cited

PUBLICATIONS

World Intellectual Property Organization PCT International Search and Preliminary Examination Guidelines published 2004 (Year: 2004).*
Brown DW, "The Evolution of Fosfomycin Resistance Enzyme, FosA, from Pseudomonas aeruginosa and the Development of a High-Throughput Screen for the Discovery of Bioactive Inhibitors," (Dissertation) May 10, 2010. Retrieved from URL: http://etd.library.vanderbilt.edu/ available/etd-05242010-103718/, May 10, 2010, 74 pp.
Brown, et al. "Evolution of the Antibiotic Resistance Protein, FosA, is Linked to a Catalytically Promiscuous Progenitor," *Biochemistry* Mar. 10, 2009, 48(9):1845-1849, author manuscript, 10 pp.
CAS Registry No. 1092683-25-4; CA Index Name: Pyrazolo[1,5-a]pyrimidin-2(1H)-one, 6,6'-(4-nitro-1H-pyrazole-3,5-diyl)bis[3-chloro-; Entered STN: Jan. 6, 2009. Jan. 6, 2009.
CAS Registry No. 1039121-51-1; CA Index Name: Pyrazolo[1,5-a]pyrimidin-2(1H)-one, 6-[3-( 1,2-dihydro-3-nitro-2-oxopyrazolo[ 1,5-a]pyrimidin-6-yl)-4-nitro-1 H-pyrazol-5-yl]-3-nitro-; Entered STN: Aug. 7, 2008. Aug. 7, 2008.
International Search Report and Written Opinion, dated Apr. 15, 2018, issued in corresponding International Application No. PCT/US2018/013282.
Rigsby RE et al., "Phosphonoformate: a minimal transition state analogue inhibitor of the fosfomycin resistance protein, FosA.," *Biochemistry*. Nov. 2, 2004; 43(43), pp. 13666-13673. Retrieved from URL: <http://booksc.org/book/30225535/de633d>. Nov. 2, 2004 (Nov. 2, 2004) Abstract only.
Sastry S and Doi Y., "Fosfomycin: resurgence of an old companion," *Journal of Infection and Chemotherapy*. May 1, 2016; 22(5), pp. 273-280. Retrieved from URL: <https://www.ncbi.nlm.nih.gov/pmc/articles/PMC4833629/pdf/nihms758740.pdf>. May 1, 2016(May 1, 2016).

* cited by examiner

*Primary Examiner* — Timothy P Thomas
*Assistant Examiner* — George W Kosturko
(74) *Attorney, Agent, or Firm* — Klarquist Sparkman, LLP

(57) ABSTRACT

Compounds, pharmaceutical compositions, and methods for reversing fosfomycin resistance are disclosed. Embodiments of the disclosed compounds inhibit fosfomycin-inhibiting enzymes. Some embodiments of the compounds are FosA inhibitors. The disclosed pharmaceutical compositions include (i) fosfomycin or a pharmaceutically acceptable salt thereof and (ii) a compound, or a pharmaceutically acceptable salt thereof, which inhibits a fosfomycin-inhibiting enzyme. A method of inhibiting growth of a fosfomycin-resistant bacterium includes contacting the bacterium with (i) fosfomycin or a pharmaceutically acceptable salt thereof and (ii) an effective amount of a disclosed compound or a pharmaceutically acceptable salt thereof.

16 Claims, 18 Drawing Sheets

FIG. 1

| Compound | IC$_{50}$ (µM) |
|---|---|
| ANY1 | 5 |
| ANY2 | 100 |
| ANY3 | >500 |
| ANY4 | >500 |
| ANY5 | >500 |
| ANY6 | >500 |
| ANY7 | >500 |
| ANY8 | >500 |
| ANY9 | >500 |

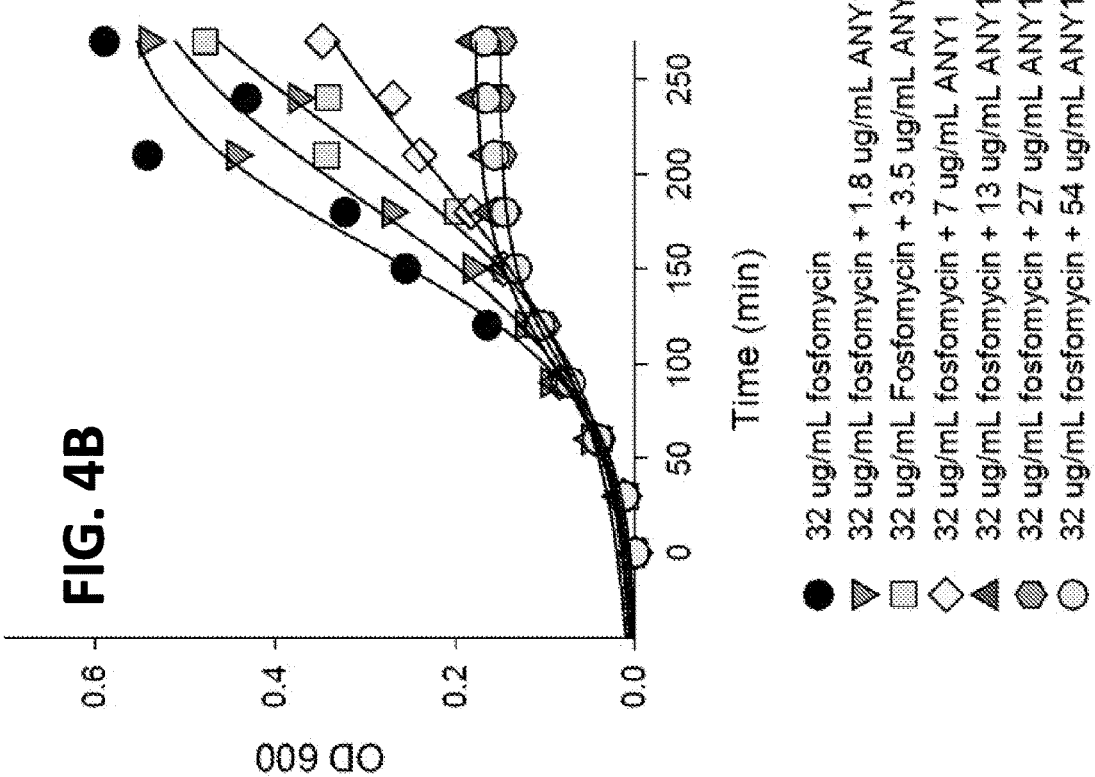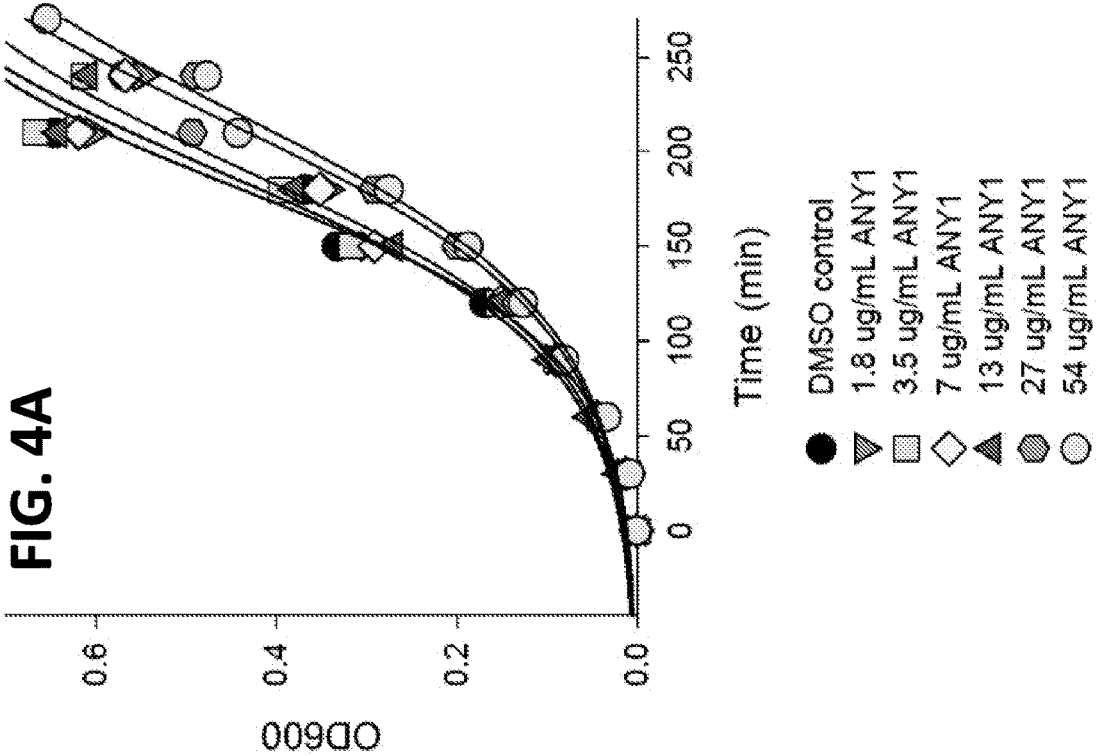

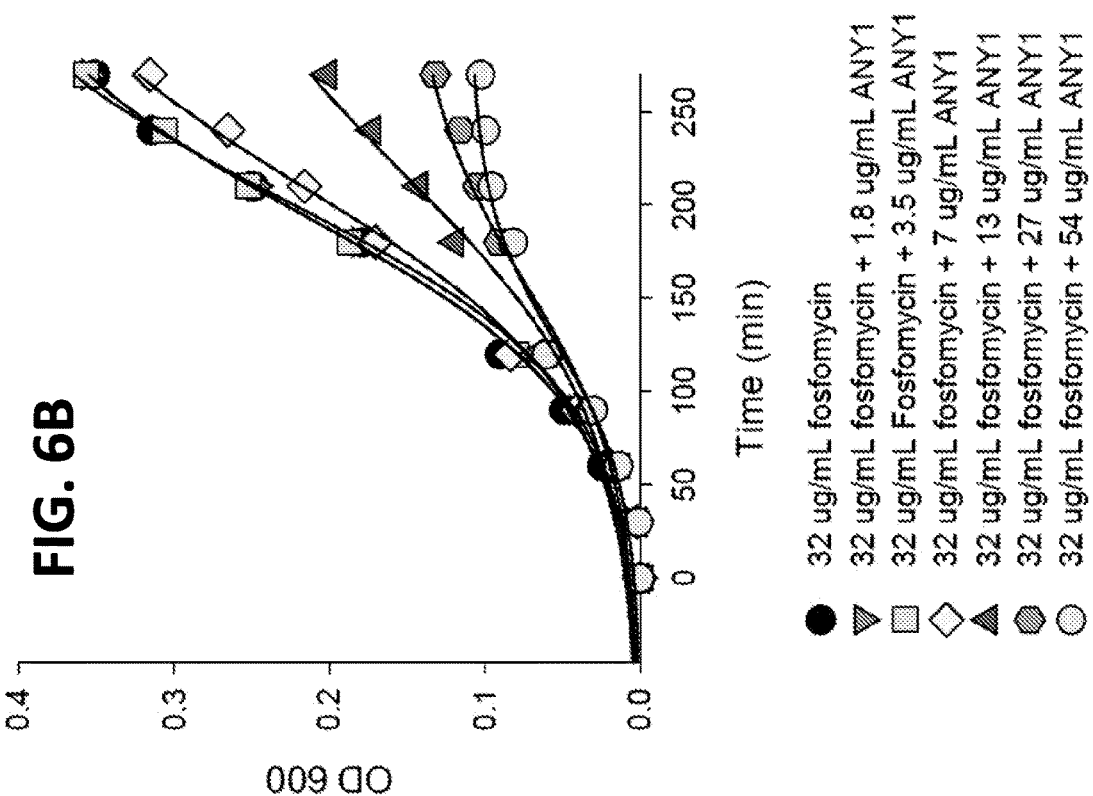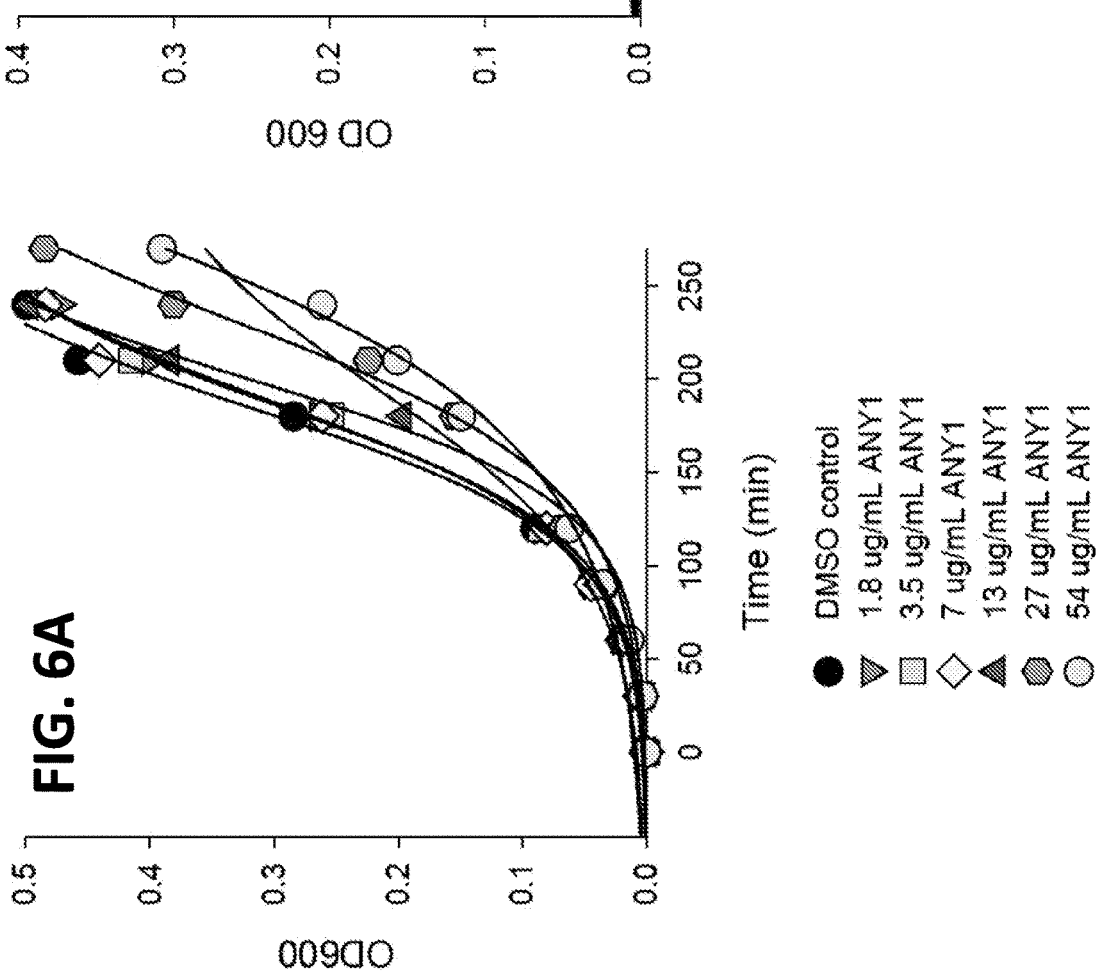

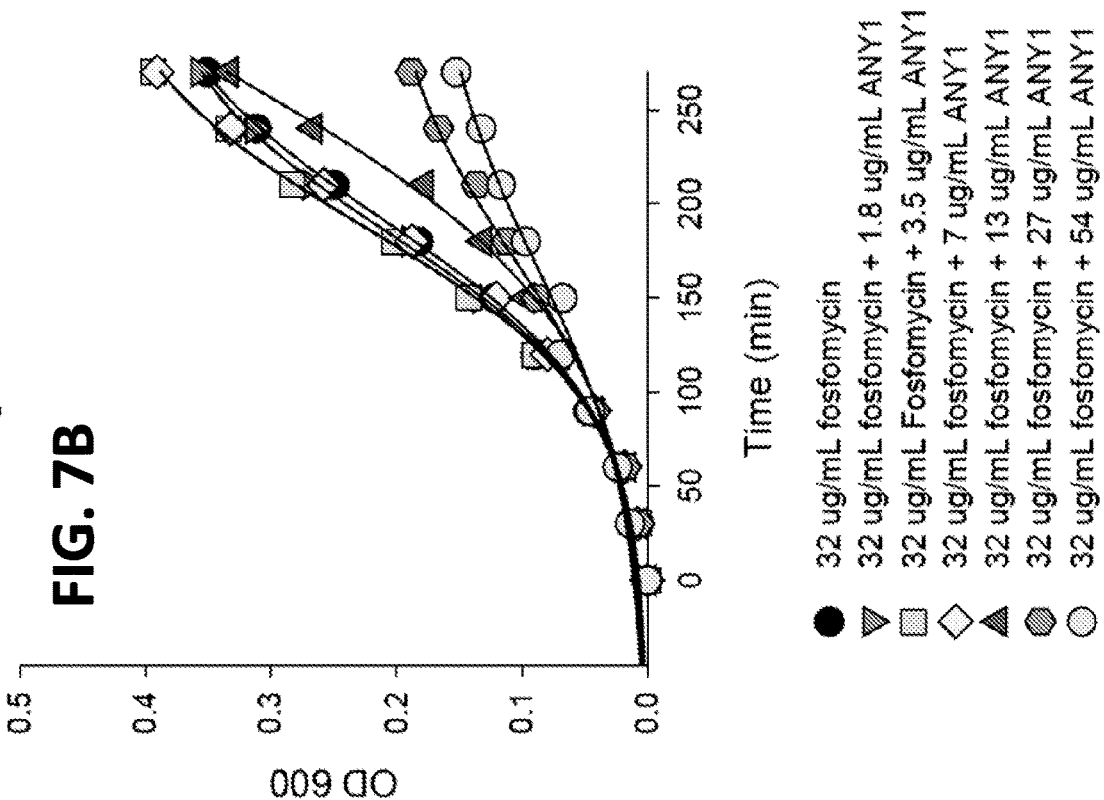
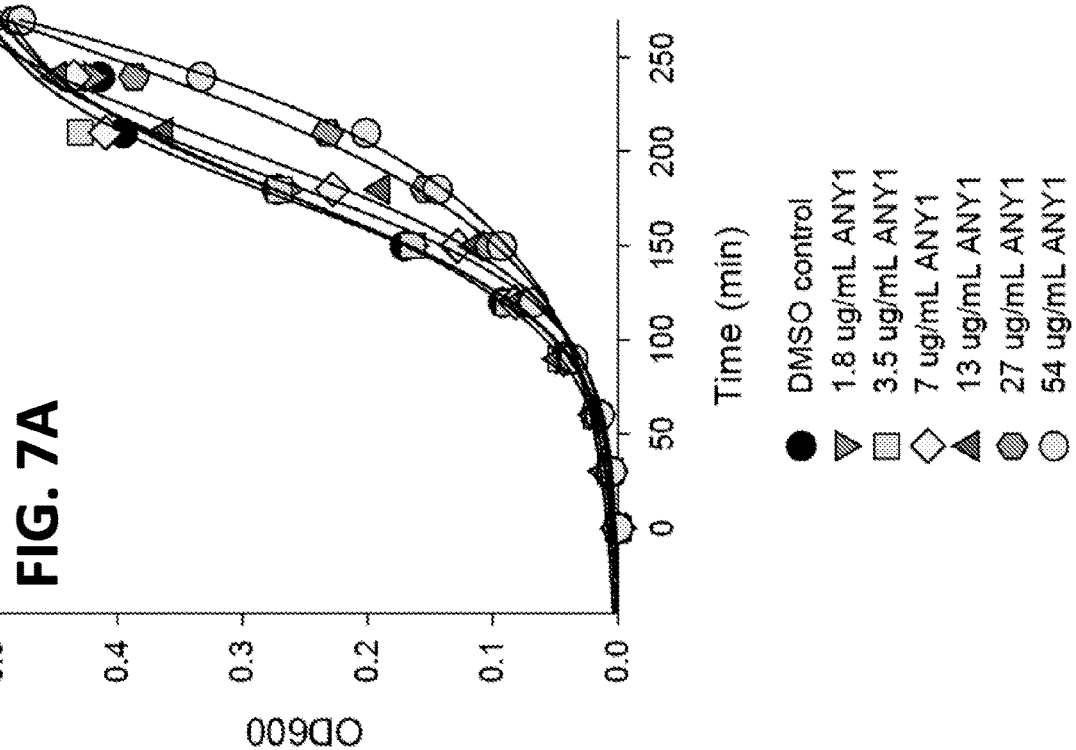

FIG. 9

| Parameter | Value for: Apo FosA3 | Holo FosA$^{KP}$ | Apo FosA$^{KP}$ |
|---|---|---|---|
| Data collection statistics | | | |
| Resolution range | 29.44–2.689 (2.785–2.689) | 28.27–1.539 (1.594–1.539) | 28.69–1.3 (1.346–1.3) |
| Space group | P 41 2 2 | P 21 21 21 | P 2 21 21 |
| Unit cell (a, b, c, α, β, γ) | 87.608, 87.608, 357.038, 90, 90, 90 | 40.071, 47.155, 149.517, 90, 90, 90 | 44.875, 67.54, 89.508, 90, 90, 90 |
| No. of: | | | |
| Total reflections | 376,188 (37,524) | 183,460 (17,829) | 349,328 (7,547) |
| Unique reflections | 39,913 (3,873) | 41,623 (4,170) | 60,254 (3,033) |
| Multiplicity | 9.4 (9.7) | 4.4 (4.3) | 5.8 (2.5) |
| Completeness (%) | 1.00 (1.00) | 0.97 (0.99) | 0.89 (0.46) |
| Mean I/sigma I | 20.50 (3.15) | 14.74 (2.22) | 19.77 (2.32) |
| Wilson B-factor | 57.2 | 17.87 | 12.51 |
| $R_{merge}$ | 0.0800 (0.6252) | 0.0509 (0.6815) | 0.04812 (0.3153) |
| $R_{meas}$ | 0.0847 (0.6605) | 0.0577 (0.7737) | 0.0525 (0.4066) |
| CC1/2 | 0.999 (0.951) | 0.999 (0.924) | 0.999 (0.837) |
| CC* | 1 (0.987) | 1 (0.98) | 1 (0.955) |
| Refinement | | | |
| Reflections used in refinement | 39,869 (3,864) | 41,577 (4,164) | 60,246 (3,031) |
| No. of reflections used for $R_{free}$ | 1,918 (185) | 2,065 (214) | 3,094 (162) |
| $R_{work}$ | 0.2051 (0.2963) | 0.1682 (0.2709) | 0.1254 (0.1772) |
| $R_{free}$ | 0.2493 (0.3524) | 0.2059 (0.3171) | 0.1491 (0.2142) |
| CC(work) | 0.947 (0.872) | 0.967 (0.947) | 0.977 (0.941) |
| CC(free) | 0.913 (0.732) | 0.952 (0.906) | 0.971 (0.921) |
| No. of: | | | |
| Nonhydrogen atoms | 8,600 | 2,480 | 2,624 |
| Macromolecules | 8,586 | 2,372 | 2,220 |
| Ligands | 14 | 31 | 2 |
| Protein residues | 1,091 | 275 | 276 |
| Water molecules | 0 | 277 | 402 |
| RMSD | | | |
| Bond length (Å) | 0.006 | 0.006 | 0.007 |
| Angles (°) | 0.97 | 0.78 | 0.91 |
| Average B-factor | 65.61 | 29.5 | 17.27 |

*aOverall values are reported, with highest-resolution shell values in parentheses.*

FIG. 11

| Pathogen | 6 | 9 | 34 | 36 | 39 | 46 | 48 | 65 | 67 | 96 | 113 | 122 | 131 |
|---|---|---|---|---|---|---|---|---|---|---|---|---|---|
| | | | | | | Residue # | | | | | | | |
| P. stuartii | H | T | W | R | Y | W | C | Y | H | R | E | R | Y |
| S. marcescens | H | T | W | G | Y | W | C | Y | H | R | E | R | Y |
| E. aerogenes | H | T | W | S | Y | W | C | Y | H | R | E | R | Y |
| K. oxtoca | H | T | W | N | Y | W | C | Y | H | K | E | R | Y |
| M. morganii | H | T | W | Y | Y | W | C | Y | H | R | E | R | Y |
| K. pneumoniae | H | T | W | S | Y | W | C | Y | H | R | E | R | Y |
| E. cloacae | H | T | W | T | Y | W | C | Y | H | K | E | R | Y |
| P. aeruginosa | H | T | W | Q | Y | W | C | Y | H | R | E | R | Y |
| E. coli (A3) | H | T | W | S | Y | W | C | Y | H | R | E | R | Y |

Scheme 3

REVERSAL OF FOSFOMYCIN RESISTANCE

CROSS REFERENCE TO RELATED APPLICATIONS

This is the U.S. National Stage of International Application No. PCT/US2018/013282, filed Jan. 11, 2018, which was published in English under PCT Article 21(2), which in turn claims the benefit of U.S. Provisional Application No. 62/445,662, filed Jan. 12, 2017, each of which is herein incorporated by reference in its entirety.

ACKNOWLEDGMENT OF GOVERNMENT SUPPORT

This invention was made with government support under AI123747 awarded by the National Institutes of Health. The government has certain rights in the invention.

FIELD

This invention pertains to compounds, pharmaceutical compositions, and methods for reversing fosfomycin resistance of bacteria expressing fosfomycin-modifying enzymes.

BACKGROUND

Fosfomycin (also known as phosphomycin or phosphonomycin) is a broad-spectrum antibiotic produced by some *Streptomyces* species (e.g., *S. fradiae, S. lividans*) or by synthetic means. Fosfomycin covalently binds to the active site of UDP-N-acetylglucosamine enolpyruvyl transferase (MurA) of both Gram-negative and Gram-positive bacteria, and inhibits synthesis of the bacterial peptidoglycan precursor UDP N-acetylmuramic acid.

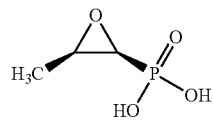

Fosfomycin

Fosfomycin, which was discovered over four decades ago, has drawn renewed interest as an agent active against multidrug-resistant (MDR) and extensively drug-resistant (XDR) pathogens. In a review of 17 studies that evaluated the antimicrobial activity and clinical effectiveness of fosfomycin for infections caused by MDR Enterobacteriaceae, including ESBL producing organisms, 11 studies reported that at least 90% of the isolates were susceptible to fosfomycin. There is also a growing interest in potential use of fosfomycin for the treatment of infections caused by carbapenem-resistant Enterobacteriaceae, such as KPC-producing *Klebsiella pneumoniae*. In the U.S., fosfomycin tromethamine is approved as a single-dose, orally administered treatment for cystitis. In several European and Asian countries, an intravenous fosfomycin disodium formulation is available, and is used to treat bacteremia, pneumonia, urinary tract infection, osteomyelitis and central nervous system infections, usually in combination with another active agent. A clinical trial evaluating the safety and efficacy of intravenous FOM for the treatment of complicated urinary tract infection and acute pyelonephritis has been completed in the U.S. (NCT02753946; clinicaltrials.gov), with likely FDA approval in early 2018. However, with increased use of fosfomycin, there is increased risk of fosfomycin resistance. Thus, there is a need for compounds and methods to reverse fosfomycin resistance.

SUMMARY

This disclosure concerns compounds, pharmaceutical compositions and methods for reversing fosfomycin resistance of bacteria expressing fosfomycin-modifying enzymes. In some embodiments, the compound has a structure according to Formula A, or a stereoisomer, tautomer, or pharmaceutically acceptable salt thereof.

Formula A

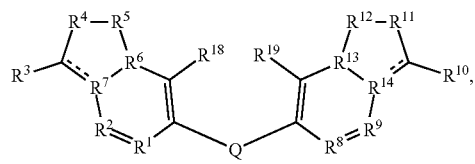

wherein each bond indicated with " $=\!=\!=$ " is a single bond or a double bond as needed to satisfy valency requirements; $R^1$, $R^2$, $R^8$, and $R^9$ independently are N, C(OH), C(SH), C(CH$_3$), C(CFH$_2$), C(CF$_2$H), or C(CF$_3$); $R^3$ and $R^{10}$ independently are Br, F, Cl, OH, SH, NH$_2$, NO$_2$, alkyl, haloalkyl, or aryl; $R^4$ and $R^{11}$ independently are C=O, C=S, C(H)CH$_3$, C(H)CFH$_2$, C(H)CF$_2$H, C(H)CF$_3$, SO$_2$, SO, COOR' where R' is H or C$_1$-C$_5$ alkyl, or COO$^-$; $R^5$ and $R^{12}$ independently are NR' where R' is H or C$_1$-C$_5$ alkyl, O, S, CH$_2$, C(H)OH, C(H)SH, C(H)CH$_3$, C(H)CFH$_2$, C(H)CF$_2$H, or C(H)CF$_3$; $R^6$ and $R^{13}$ independently are N or CH; $R^7$ and $R^{14}$ independently are N or C; $R^{18}$ and $R^{19}$ independently are H or C$_1$-C$_5$ alkyl; and Q is

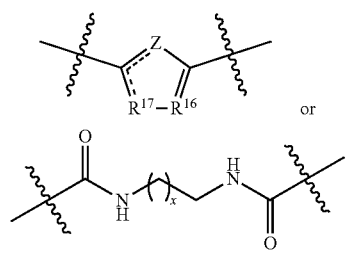

where x is 1, 2, 3, 4, or 5, each bond indicated with " $=\!=\!=$ " is a single bond or a double bond as needed to satisfy valency requirements, Z is CR$^{15}$, S, N, or O, where R$^{15}$ is H, NO$_2$, COO$^-$, COOR', CN, CS$_2$, CH$_3$, CFH$_2$, CF$_2$H, CF$_3$, or SO$_2$CF$_3$, where R' is H or C$_1$-C$_5$ alkyl, R$^{16}$ is N, CH, C(OH), C(SH), C(CH$_3$), C(CFH$_2$), C(CF$_2$H), or C(CF$_3$), and R$^{17}$ is NH, N(CH$_3$), N, O, S, CH, CH$_2$, C(H)OH, C(H)SH, C(H)CH$_3$, C(H)CFH$_2$, C(H)CF$_2$H, or C(H)CF$_3$.

In some embodiments, the compound has a structure according to Formula I, or a stereoisomer, tautomer, or pharmaceutically acceptable salt thereof

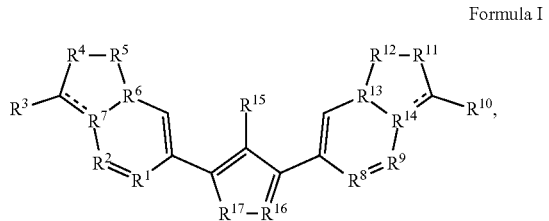

Formula I wherein each bond indicated with " ═══ " is a single bond or a double bond as needed to satisfy valency requirements; $R^1$, $R^2$, $R^8$, $R^9$ and $R^{16}$ independently are N, C(OH), C(SH), C(CFH$_2$), C(CF$_2$H), or C(CF$_3$); $R^3$ and $R^{10}$ independently are Br, F, Cl, OH, SH, NH$_2$, NO$_2$, CH$_3$, CFH$_2$, CF$_2$H, or CF$_3$; $R^4$ and $R^{11}$ independently are C═O, C═S, C(H)CFH$_2$, C(H)CF$_2$H, C(H)CF$_3$, SO$_2$, or SO; $R^5$, $R^{12}$, and $R^{17}$ independently are NH, NCH$_3$, O, S, CH$_2$, C(H)OH, C(H)SH, C(H)CFH$_2$, C(H)CF$_2$H, or C(H)CF$_3$; $R^6$ and $R^{13}$ independently are N or CH; $R^7$ and $R^{14}$ independently are N or C; and $R^{15}$ is NO$_2$, COO, CN, CS$_2$, CFH$_2$, CF$_2$H, or CF$_3$. The pharmaceutical composition may further comprise a pharmaceutically acceptable carrier.

In one embodiment, the compound is

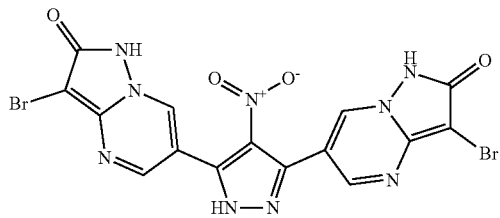 [SMILES: O=c1[nH]n2cc(-c3n[nH]c(-c4cnc5c(Br)c(=O)[nH]n5c4)c3[N+](=O)[O-])cnc2c1Br]

3-bromo-6-[3-(3-bromo-2-oxo-1H-pyrazolo[1,5-a]pyrimidin-6-yl)-4-nitro-1H-pyrazol-5-yl]-1H-pyrazolo[1,5-a]pyrimidin-2-one.

In an independent embodiment, the compound is

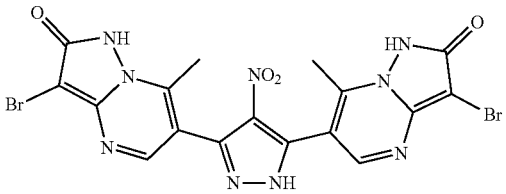 [SMILES: Cc1c(-c2n[nH]c(-c3cnc4c(Br)c(=O)[nH]n4c3C)c2[N+](=O)[O-])cnc2c(Br)c(=O)[nH]n12]

6,6'-(4-nitro-1H-pyrazole-3,5-diyl)bis(3-bromo-7-methylpyrazolo[1,5-a]pyrimidin-2(1H)-one).

Embodiments of a pharmaceutical composition for reversing fosfomycin resistance include fosfomycin or a pharmaceutically acceptable salt thereof and a compound according to Formula A or Formula I. The pharmaceutical composition may further include a pharmaceutically acceptable carrier.

Embodiments of a method for inhibiting growth of a fosfomycin-resistant bacterium including contacting a fosfomycin-resistant bacterium with (i) fosfomycin or a pharmaceutically acceptable salt thereof and (ii) an effective amount of a compound according to Formula A or Formula I or a pharmaceutically acceptable salt thereof according to any of the above embodiments. In some embodiments, the fosfomycin-resistant bacterium is a bacterium that produces a FosA enzyme. In certain embodiments, the fosfomycin-resistant bacterium is a Gram-negative bacterium. Exemplary fosfomycin-resistant bacteria include *Enterobacter cloacae*, *Klebsiella pneumoniae*, *Pseudomonas aeruginosa*, and *Escherichia coli*. In any or all of the foregoing embodiments, the effective amount of the compound may be within a range of 5 µM to 20 µM.

In any or all of the above embodiments, contacting the fosfomycin-resistant bacterium may be performed in vivo. In some embodiments, contacting the fosfomycin-resistant bacterium comprises administering a therapeutically effective amount of fosfomycin or pharmaceutically acceptable salt thereof and the effective amount of the compound or pharmaceutically acceptable salt thereof to a subject identified as having, or being at risk of having, an infection caused by a fosfomycin-resistant bacterium. In any or all of the foregoing embodiments, administering the therapeutically effective amount of fosfomycin or pharmaceutically acceptable salt thereof and the effective amount of the compound or pharmaceutically acceptable salt thereof may be performed simultaneously or sequentially in any order. In any or all of the foregoing embodiments, administering the therapeutically effective amount of fosfomycin or pharmaceutically acceptable salt thereof and the effective amount of the compound or pharmaceutically acceptable salt thereof may include administering an amount of a pharmaceutical composition comprising the therapeutically effective amount of fosfomycin or pharmaceutically acceptable salt thereof and the effective amount of the compound or pharmaceutically acceptable salt thereof. In any or all of the foregoing embodiments, the compound may be 3-bromo-6-[3-(3-bromo-2-oxo-1H-pyrazolo[1,5-a]pyrimidin-6-yl)-4-nitro-1H-pyrazol-5-yl]-1H-pyrazolo[1,5-a]pyrimidin-2-one, and the effective amount is an amount sufficient to provide an in vivo concentration within a range of 5 µM to 20 µM.

The foregoing and other objects, features, and advantages of the invention will become more apparent from the following detailed description, which proceeds with reference to the accompanying figures.

BRIEF DESCRIPTION OF THE DRAWINGS

FIG. 1 shows the concentration of 3-bromo-6-[3-(3-bromo-2-oxo-1H-pyrazolo[1,5a]pyrimidin-6-yl)-4-nitro-1H-pyrazol-5-yl]-1H-pyrazolo[1,5-a]pyrimidin-2-one ("ANY1") required to inhibit FosA enzyme activity by 50% in vitro; the activity of several structural analogs is also shown.

FIGS. 4A and 4B are graphs showing the inhibitory activity of ANY1 at various concentrations towards fosfomycin-resistant, FosA-producing *Enterobacter cloacae* in the absence (FIG. 4A) and presence (FIG. 4B) of 32 µg/mL fosfomycin.

FIGS. 6A and 6B are graphs showing the inhibitory activity of ANY1 at various concentrations towards fosfomycin-resistant, FosA-producing *Pseudomonas aeruginosa* in the absence (FIG. 6A) and presence (FIG. 6B) of 32 µg/mL fosfomycin.

FIGS. 7A and 7B are graphs showing the inhibitory activity of ANY1 at various concentrations towards fosfomycin-resistant, FosA-producing *Escherichia coli* in the absence (FIG. 7A) and presence (FIG. 7B) of 32 μg/mL fosfomycin.

FIG. 9 is a table of the data collection and refinement statistics used in determining the crystal structures of Apo FosA3, Holo FosA$^{KP}$, and Apo FosA$^{KP}$.

FIG. 10A shows two molecules of FosA$^{KP}$, a dimer with two independent active sites; two molecules of ANY1 bind per FosA dimer. FIG. 10B illustrates the protein-ANY1 interactions at the FosA$^{KP}$ active site. FIG. 10C is an overlay of fosfomycin and ANY1 in the FosA$^{KP}$ active site. FIG. 10D shows drug-drug and drug-protein interactions between two molecules of FosA$^{KP}$.

FIG. 11 shows sequence alignment of FosA residues involved in ANY1 binding across enzymes from different bacterial species.

DETAILED DESCRIPTION

Figure 2:
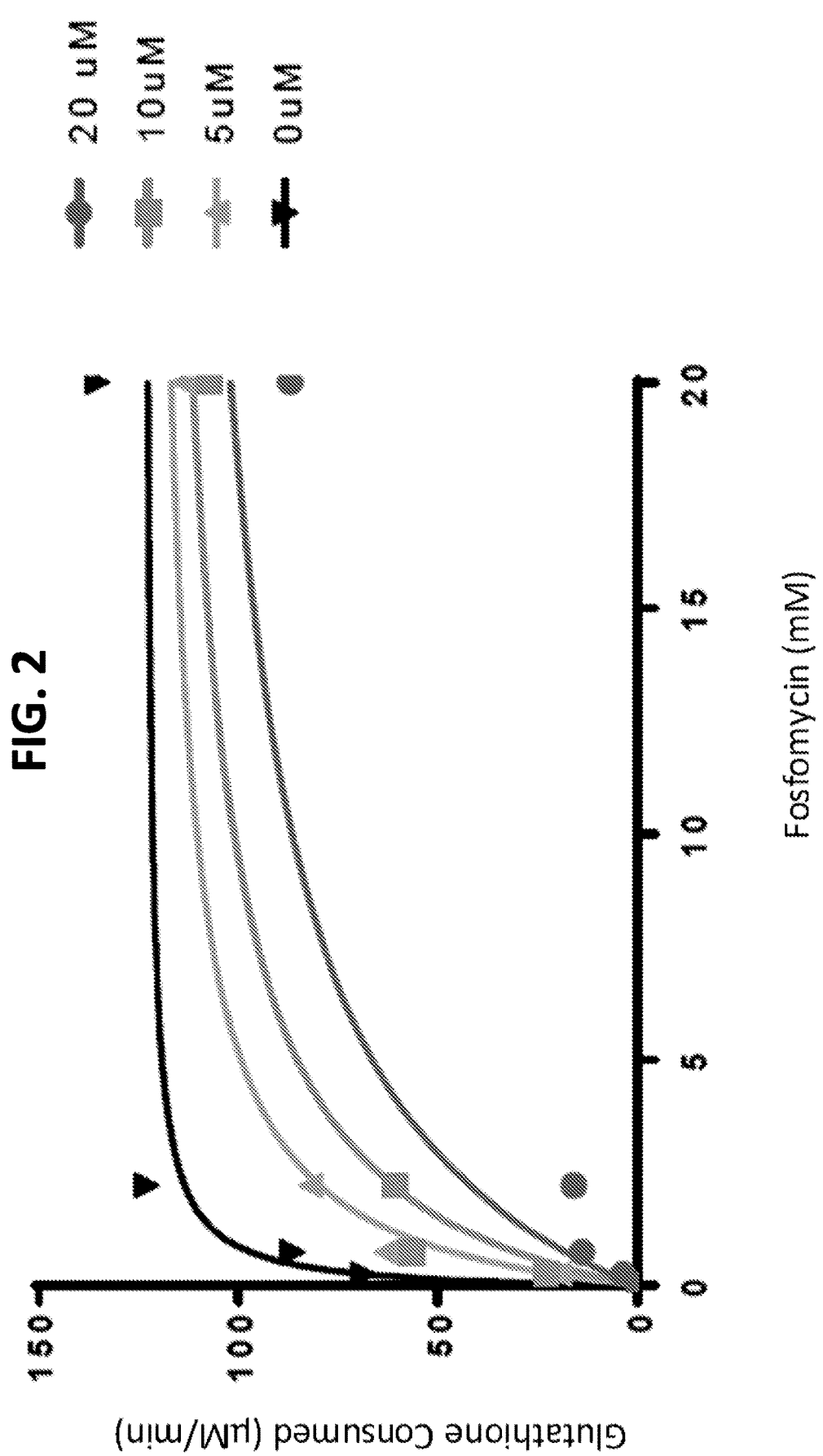
FIG. 2 is a graph showing steady-state kinetics of ANY1 inhibition of FosA activity.

This disclosure concerns compositions and methods for reversing fosfomycin resistance. The compositions include compounds that inhibit fosfomycin-inhibiting enzymes that are either chromosomally-encoded or transferred through plasmids. Some embodiments of the disclosed compounds are FosA inhibitors. Methods of using the compounds to inhibit fosfomycin-resistant bacteria are also disclosed.

I. Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

FOM: Fosfomycin

GST: Glutathione S transferase

IC$_{50}$: Half maximal inhibitory concentration, i.e., the concentration of an active agent required to inhibit a biological process by half.

Minimum inhibitory concentration (MIC): The lowest concentration of an active agent that will inhibit visible growth of a microorganism after overnight incubation.

Pharmaceutically acceptable carrier: The pharmaceutically acceptable carriers (vehicles) useful in this disclosure are conventional. Remington: *The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compositions and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some examples, the pharmaceutically acceptable carrier is a non-naturally occurring or synthetic carrier. The carrier also can be formulated in a unit-dosage form that carries a preselected therapeutic dosage of the active agent, for example in a pill, vial, bottle, or syringe.

Pharmaceutically acceptable salt: A biologically compatible salt of a compound that can be used as a drug, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, benzene sulfonic acid (besylate), cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Stereoisomers: Isomers that have the same molecular formula and sequence of bonded atoms, but which differ only in the three-dimensional orientation of the atoms in space. Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture." E/Z isomers are isomers that differ in the stereochemistry of a double bond. An E isomer (from entgegen, the German word for "opposite") has a trans-configuration at the double bond, in which the two groups of highest priority are on opposite sides of the double bond. A Z isomer (from zusammen, the German word for "together") has a cis-configuration at the double bond, in which the two groups of highest priority are on the same side of the double bond.

Tautomers: Constitutional isomers of organic compounds that differ only in the position of the protons and electrons, and are interconvertible by migration of a hydrogen atom. Tautomers ordinarily exist together in equilibrium.

Therapeutically effective amount (or dose): An amount sufficient to provide a beneficial, or therapeutic, effect to a subject or a given percentage of subjects.

Treating or treatment: With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

II. Overview of Fosfomycin and Fosfomycin-Modifying Enzymes

Fosfomycin (FOM) is highly active against *E. coli*, including those producing extended-spectrum beta-lactamases (ESBL), with $MIC_{50}$ and $MIC_{90}$ values (minimum inhibitory concentrations that inhibit 50% and 90% of the isolates, respectively) generally falling between 2 and 4 μg/mL (the CLSI (Clinical and Laboratory Standards Institute) and EUCAST (European Committee on Antimicrobial Susceptibility Testing) susceptibility breakpoints are 64 and 32 μg/mL, respectively). However, for ESBL- and carbapenemase-producing *Klebsiella pneumoniae*, the $MIC_{50}$ and $MIC_{90}$ values are significantly higher (~32 and ~128 μg/mL, respectively), translating to decreased susceptibility rates (Sastry et al., *J Infect Chemother* 2016, 22:273-280). Data on other species are scarce, but *Enterobacter* spp., *Proteus* spp. and *Pseudomonas aeruginosa* also have substantially reduced susceptibility rates (Vardakas et al., *Int J Antimicrob Agents* 2016, 47:269-285). However, the CLSI susceptibility breakpoint applies only to infection in the urinary tract, where FOM concentrations of >128 μg/mL are sustained for 24-48 h after a single oral dose (Patel et al., *Drugs* 1997, 53:637-656), and concentrations in other relevant sites of infection are lower than in the urinary tract even after intravenous dosing (Falagas et al., *Clin Microbiol Rev* 2016, 29:321-347). This suggests that: i) the activity of FOM alone may not be sufficient in treating systemic infections caused by Gram-negative bacteria other than *E. coli*; and ii) a pharmacological approach to lower FOM MICs has the potential to expand its activity to a broader spectrum of Gram-negative pathogens.

There are three major classes of fosfomycin-modifying enzymes (FosA, FosB, and FosX) capable of conferring fosfomycin-resistance in pathogens. FosA is the group of enzymes most frequently reported among Gram-negative bacteria. As shown in Scheme 1, FosA is a dimeric $K^+$- and $Mn^{2+}$-dependent glutathione S-transferase (GST) that catalyzes the nucleophilic addition of glutathione to carbon atom 1 of fosfomycin to open the epoxide ring, thereby rendering the drug inactive.

Scheme 1

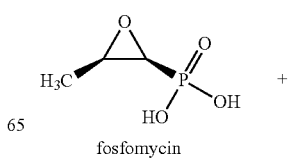

fosfomycin

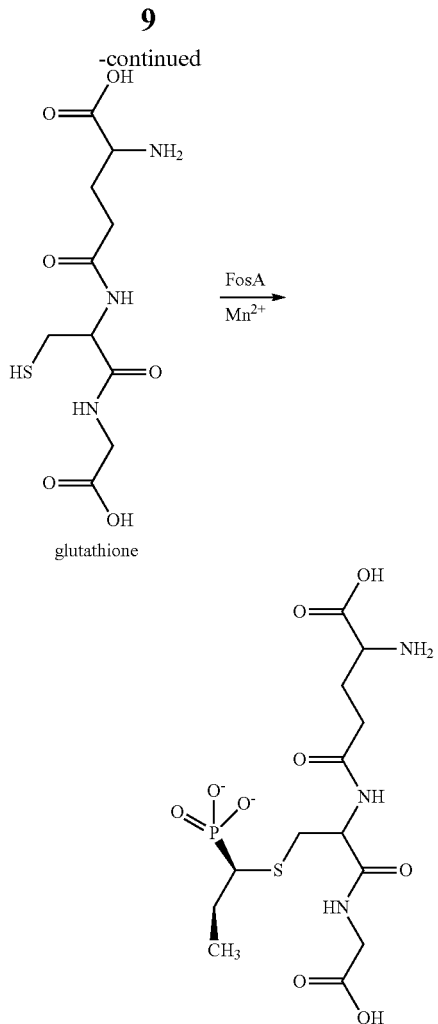

glutathione

Plasmid-borne FosA variants (e.g. FosA3) have been reported in FOM-resistant *E. coli*. However, the prevalence and distribution of FosA in other Gram-negative bacteria varies. Table 1 summarizes the presence of FosA in Gram-negative bacteria in over 18,000 published genomes from 18 species (Ito et al., *MBio* 2017, 8(4) pii: e00749-17). It was found that FosA was frequently identified in the genomes of *Providencia stuartii* (100%), *K. pneumoniae* (99.7%), *Serratia marcescens* (99.7%), *Enterobacter aerogenes* (97.5%), *P. aeruginosa* (98.8%), *K. oxytoca* (96.6%), *Morganella morganii* (90.5%), *P. rettgeri* (85.7%) and *E. cloacae* (82.4%). In contrast, FosA was rarely identified in other species including *E. coli* (4.3%). FosA amino acid sequences in different bacterial pathogens are divergent, but key residues in the active site are highly conserved.

TABLE 1

| Species | Number of genomes | Frequency of FosA (%) | MIC (µg/mL) |
| --- | --- | --- | --- |
| *Providencia stuartii* | 10 | 100 | >1024 |
| *Klebsiella pneumoniae* | 1,631 | 99.7 | >1024 |
| *Serratia marcescens* | 311 | 99.7 | >1024 |
| *Enterobacter aerogenes* | 122 | 97.5 | >1024 |
| *Pseudomonas aeruginosa* | 2,257 | 98.8 | 16 |
| *Klebsiella oxytoca* | 89 | 96.6 | >1024 |
| *Morganella morganii* | 21 | 90.5 | >1024 |
| *Providencia rettgeri* | 7 | 85.7 | >1024 |
| *Enterobacter cloacae* | 489 | 82.4 | >1024 |

TABLE 1-continued

| Species | Number of genomes | Frequency of FosA (%) | MIC (µg/mL) |
| --- | --- | --- | --- |
| *Proteus mirabilis* | 60 | 16.7 | 9.8 |
| *Salmonella enterica* | 5416 | | |
| *Acinetobacter pittii* | 104 | 7.8 | |
| *Escherichia coli* | 5,366 | 4.3 | |
| *Citrobacter freundii* | 78 | 3.8 | |
| *Acinetobacter baumannii* | 1,916 | 2.0 | |
| *Achromobacter xylosxidans* | 35 | 0 | |

These chromosomal FosA genes were found high-level FOM resistance when expressed in *E. coli*. Deletion and complementation of chromosomal FosA in *S. marcescens* eliminated and restored FOM resistance, respectively. Collectively, these data show FosA is encoded by many clinically relevant Gram-negative species and confers intrinsic FOM resistance.

Human GSTs are a superfamily of enzymes involved in phase II detoxification. However, human GSTs cannot metabolize FOM and, unlike FosA, are not $K^+$- or $Mn^{2+}$-dependent enzymes (Armstrong et al., *Chem Res Toxicol* 1997 10:2-18; Armstrong, *Curr Opin Chem Biol* 1998, 2:618-623). Additionally, their tertiary and quaternary structures differ from bacterial FosA. As such, FosA represents a novel target for the development of inhibitors to expand the activity of FOM against Gram-negative pathogens, including MDR variants that intrinsically produce FosA, and *E. coli* that produce plasmid-mediated FosA. The former includes 3 of the 6 ESKAPE pathogens (*Enterobacter* spp., *P. aeruginosa* and *K. pneumoniae*), which are increasingly resistant to conventional antimicrobial agents, and for which a critical need for new treatment options exists. The latter is an emerging problem where ESBL- or carbapenemase-producing *E. coli* strains from human and animals in East Asia are acquiring fosA3 to gain resistance to FOM, with signs of spread worldwide (Sastry et al., *J Infect Chemother* 2016, 22:273-280).

III. Inhibitors of Fosfomycin-Modifying Enzymes

Embodiments of the disclosed compounds may function as inhibitors of fosfomycin-modifying enzymes, thereby reversing fosfomycin resistance, such as fosfomycin resistance in Gram-negative bacteria. In some embodiments, the compounds are FosA inhibitors. Embodiments of the disclosed compounds have a chemical structure according to general Formula A, or a stereoisomer, tautomer, or pharmaceutically acceptable salt thereof Formula A

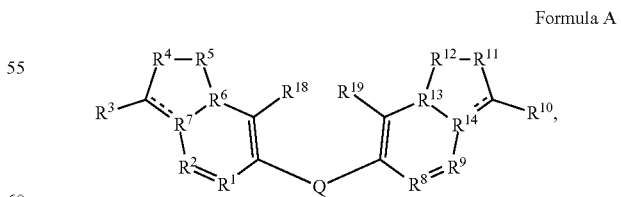

wherein each bond indicated with " ══ " is a single bond or a double bond as needed to satisfy valency requirements. $R^1$, $R^2$, $R^8$, and $R^9$ independently are N, CH, C(OH), C(SH), $C(CH_3)$, $C(CFH_2)$, $C(CF_2H)$, or $C(CF_3)$. $R^3$ and $R^{10}$ independently are Br, F, Cl, OH, SH, $NH_2$, $NO_2$, alkyl, haloalkyl, or aryl. $R^4$ and $R^{11}$ independently are C═O, C═S, C(H)

CH$_3$, C(H)CFH$_2$, C(H)CF$_2$H, C(H)CF$_3$, SO$_2$, SO, COOR' where R' is H or C$_1$-C$_5$ alkyl, or COO$^-$. R$^5$ and R$^{12}$ independently are NR' where R' is H or C$_1$-C$_5$ alkyl, O, S, CH$_2$, C(H)OH, C(H)SH, C(H)CH$_3$, C(H)CFH$_2$, C(H)CF$_2$H, or C(H)CF$_3$. R$^6$ and R$^{13}$ independently are N or CH. R$^7$ and R$^{14}$ independently are N or C. Q is

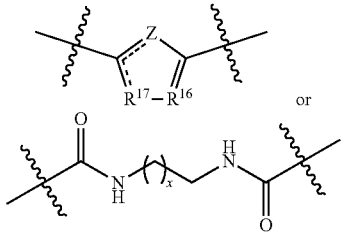

where x is 1, 2, 3, 4, or 5; each bond indicated with "═" is a single bond or a double bond as needed to satisfy valency requirements; Z is CR$^{15}$, S, N, or O, where R$^{15}$ is H, NO$_2$, COO$^-$, COOR', CN, CS$_2$, CH$_3$, CFH$_2$, CF$_2$H, CF$_3$, or SO$_2$CF$_3$, where R' is H or C$_1$-C$_5$ alkyl; R$^{16}$ is N, CH, C(OH), C(SH), C(CH$_3$), C(CFH$_2$), C(CF$_2$H), or C(CF$_3$), and R$^{17}$ is NH, N(CH$_3$), N, O, S, CH, CH$_2$, C(H)OH, C(H)SH, C(H)CH$_3$, C(H)CFH$_2$, C(H)CF$_2$H, or C(H)CF$_3$. In some embodiments, the compound is not:

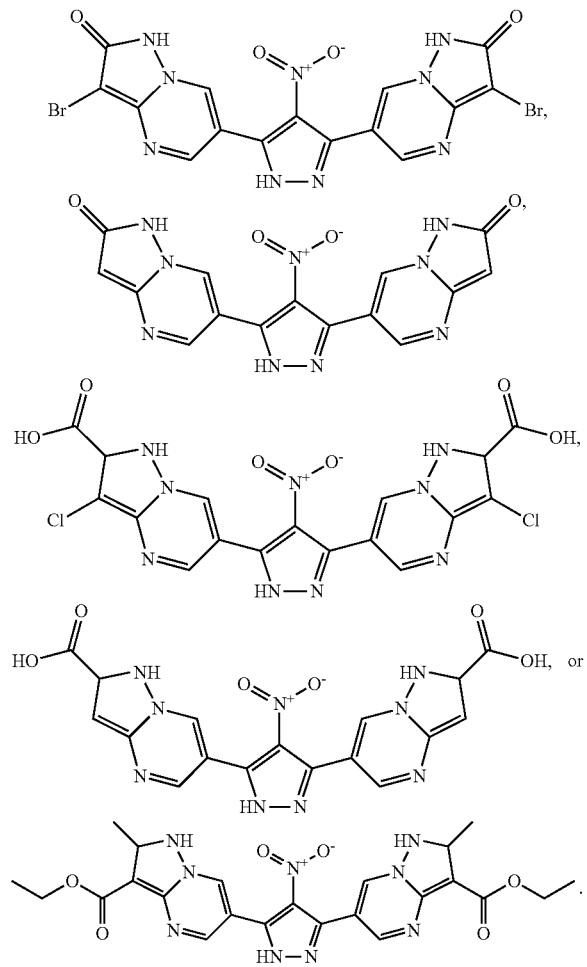

R$^1$, R$^2$, R$^8$, and R$^9$ independently are N, CH, C(OH), C(SH), C(CH$_3$), C(CFH$_2$), C(CF$_2$H), or C(CF$_3$). In some embodiments, R$^1$, R$^2$, R$^8$, and R$^9$ independently are N or CH. In certain embodiments, R$^1$ and R$^8$ are CH, and R$^2$ and R$^9$ are N.

In any or all of the above embodiments, R$^3$ and R$^{10}$ independently are Br, F, Cl, OH, SH, NH$_2$, NO$_2$, alkyl, haloalkyl, or aryl. The alkyl group may be a C$_1$-C$_5$ alkyl, e.g., methyl, ethyl, isopropyl, and the like. Alternatively, the alkyl group may be a cycloalkyl group, e.g., cyclopentyl, cyclohexyl, or cycloheptyl. The haloalkyl group may be fluoroalkyl, chloroalkyl, or bromoalkyl. Exemplary haloalkyl groups include, but are not limited to, fluoroalkyl groups, such as fluoroethyl groups, for example, C(H)CFH$_2$, C(H)CF$_2$H, and C(H)CF$_3$. The aryl group may be a 5- or 6-membered aryl group, e.g., a phenyl group. The phenyl group may be unsubstituted or substituted, e.g., substituted with an alkyl, halo, or hydroxyl group. In one embodiment, R$^3$ and R$^{10}$ are bromo. In an independent embodiment, R$^3$ and R$^{10}$ are chloro. In another independent embodiment, R$^3$ and R$^{10}$ are a hydrophobic group, such as an alkyl or aryl group, e.g., a C$_1$-C$_5$ alkyl or a phenyl group. In some embodiments, R$^3$ and R$^{10}$ independently are Br, Cl, C$_1$-C$_5$ alkyl, phenyl, F, OH, SH, NH$_2$, NO$_2$, CFH$_2$, CF$_2$H, or CF$_3$;

In any or all of the above embodiments, R$^4$ and R$^{11}$ independently are C═O, C═S, C(H)CH$_3$, C(H)CFH$_2$, C(H)CF$_2$H, C(H)CF$_3$, SO$_2$, SO, COOR' where R' is H or C$_1$-C$_5$ alkyl, or COO$^-$. In some embodiments, R$^4$ and R$^{11}$ are C═O.

In any or all of the above embodiments, R$^5$ and R$^{12}$ independently are NR' where R' is H or C$_1$-C$_5$ alkyl, O, S, CH$_2$, C(H)OH, C(H)SH, C(H)CH$_3$, C(H)CFH$_2$, C(H)CF$_2$H, or C(H)CF$_3$. In some embodiments, R$^5$ and R$^{12}$ independently are NH, NCH$_3$, O, S, CH$_2$, C(H)OH, C(H)SH, C(H)CH$_3$, C(H)CFH$_2$, C(H)CF$_2$H, or C(H)CF$_3$. In certain embodiments, R$^5$ and R$^{12}$ are NH.

In any or all of the above embodiments, R$^6$ and R$^{13}$ independently are N or CH. In some embodiments, R$^6$ and R$^{13}$ are N. In certain embodiments, R$^5$ and R$^{12}$ are NH, and R$^6$ and R$^{13}$ are N.

In any or all of the above embodiments, R$^7$ and R$^{14}$ independently are N (and the adjacent bond indicated with "═" is a single bond) or C (and the adjacent bond indicated with "═" is a double bond). In some embodiments, R$^7$ and R$^{14}$ are C.

In any or all of the above embodiments, Q is

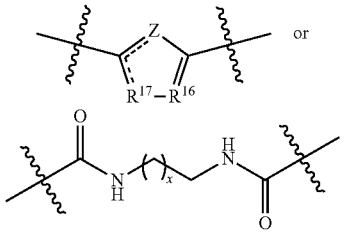

where x is 1, 2, 3, 4, or 5; each bond indicated with "═" is a single bond or a double bond as needed to satisfy valency requirements; Z is CR$^{15}$, S, N, or O, where R$^{15}$ is H, NO$_2$, COO$^-$, COOR', CN, CS$_2$, CH$_3$, CFH$_2$, CF$_2$H, CF$_3$, or SO$_2$CF$_3$, where R' is H or C$_1$-C$_5$ alkyl; R$^{16}$ is N, CH, C(OH), C(SH), C(CH$_3$), C(CFH$_2$), C(CF$_2$H), or C(CF$_3$), and R$^{17}$ is NH, N(CH$_3$), N, O, S, CH, CH$_2$, C(H)OH, C(H)SH, C(H)CH$_3$, C(H)CFH$_2$, C(H)CF$_2$H, or C(H)CF$_3$. In some embodiments, Q is

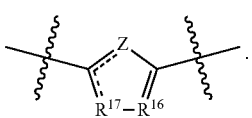

In certain embodiments, Q is

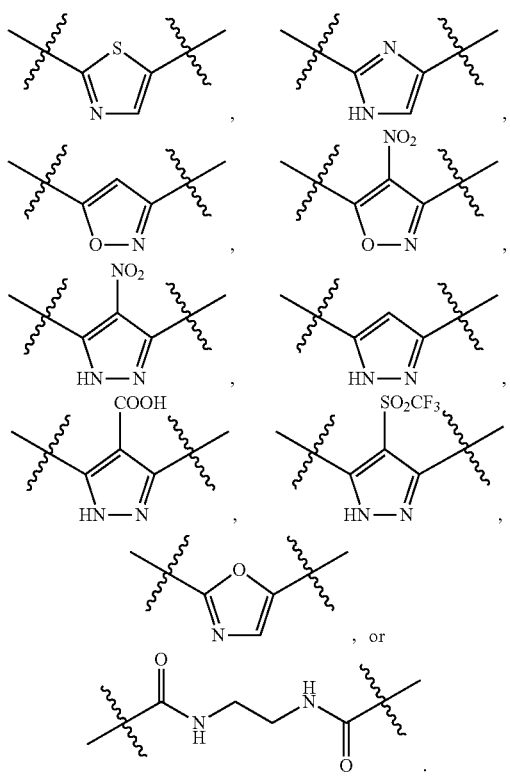

In an independent embodiment, Q is

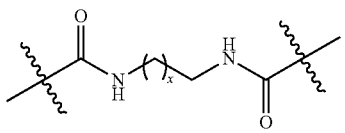

where x is 1, 2, 3, 4, or 5. In one example, Q is

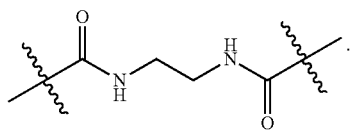 [SMILES: *C(=O)NCCNC(*)=O]

In some embodiments, (i) $R^1$ and $R^8$ are CH; (ii) $R^2$, $R^6$, $R^9$, and $R^{13}$ are N; (iii) $R^3$ and $R^{10}$ independently are Br, Cl, F, $C_1$-$C_5$ alkyl, phenyl, OH, SH, $NH_2$, $NO_2$, $CFH_2$, $CF_2H$, or $CF_3$; (iv) $R^4$ and $R^{11}$ are C(O); (v) $R^5$ and $R^{12}$ are NH; (vi) $R^6$ and $R^{13}$ are N; (vii) $R^7$ and $R^{14}$ are C; (viii) $R^{18}$ and $R^{19}$ are $CH_3$ or H; or (ix) any combination of (i), (ii), (iii), (iv), (v), (vi), (vii), and (viii) In certain embodiments, (i) $R^1$ and $R^8$ are CH; (ii) $R^2$, $R^6$, $R^9$, and $R^{13}$ are N; (iii) $R^3$ and $R^{10}$ independently are Br, Cl, $C_1$-$C_5$ alkyl or phenyl; (iv) $R^4$ and $R^{11}$ are C(O); (v) $R^5$ and $R^{12}$ are NH; (vi) $R^6$ and $R^{13}$ are N; (vii) $R^7$ and $R^{14}$ are C; (viii) $R^{18}$ and $R^{19}$ are $CH_3$; or (ix) any combination of (i), (ii), (iii), (iv), (v), (vi), (vii), and (viii) (i) $R^3$ and $R^{10}$ independently are Br, Cl, $C_1$-$C_5$ alkyl, or phenyl; (ii) $R^4$ and $R^{11}$ are C(O); (iii) $R^5$ and $R^{12}$ are NH; (iv) $R^6$ and $R^{13}$ are N; (v) $R^{18}$ and $R^{19}$ are $CH_3$; or (vi) any combination of (i), (ii), (iii), (iv), and (v). In any or all of the foregoing embodiments, Q may be

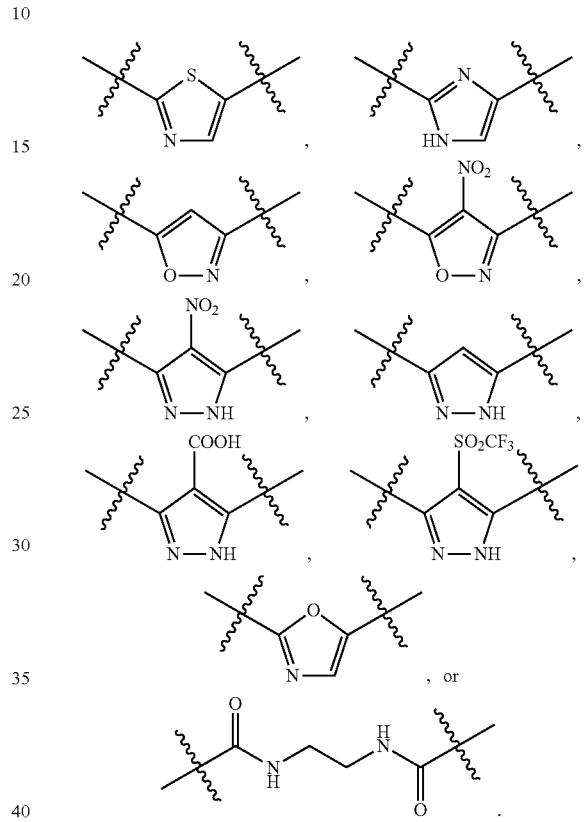

In certain of the foregoing embodiments, Q is

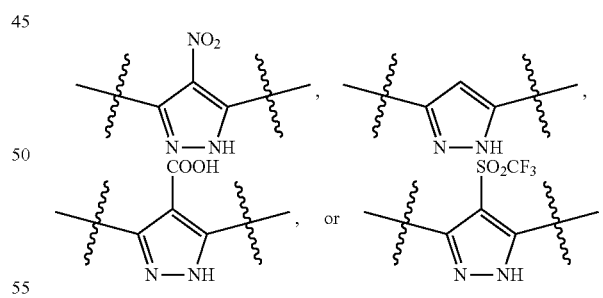

In some embodiments, the moieties on either side of Q are mirror images of one another. In other words, $R^1$ and $R^8$ are the same, $R^2$ and $R^9$ are the same, $R^3$ and $R^{10}$ are the same, $R^4$ and $R^{11}$ are the same, $R^5$ and $R^{12}$ are the same, $R^6$ and $R^{13}$ are the same, $R^7$ and $R^{14}$ are the same, and $R^{18}$ and $R^{19}$ are the same.

Some embodiments of the disclosed compounds have a chemical structure according to general Formula I, or a stereoisomer, tautomer, or pharmaceutically acceptable salt thereof:

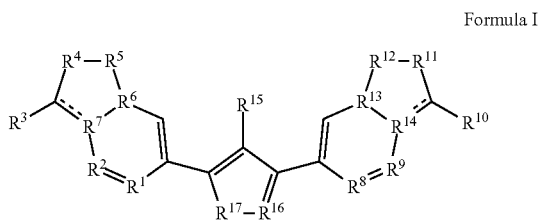

Formula I wherein bonds indicated with " --- " are single bonds or double bonds as needed to satisfy valency requirements. In general Formula I, $R^1$, $R^2$, $R^8$, $R^9$ and $R^{16}$ independently are N, CH, C(OH), C(SH), C(CFH$_2$), C(CF$_2$H), or C(CF$_3$); $R^3$ and $R^{10}$ independently are Br, F, Cl, OH, SH, NH$_2$, NO$_2$, CH$_3$, CFH$_2$, CF$_2$H, or CF$_3$; $R^4$ and $R^{11}$ independently are C=O, C=S, C(H)CFH$_2$, C(H)CF$_2$H, C(H)CF$_3$, SO$_2$, or SO; $R^5$, $R^{12}$, and $R^{17}$ independently are NH, NCH$_3$, O, S, CH$_2$, C(H)OH, C(H)SH, C(H)CFH$_2$, C(H)CF$_2$H, or C(H)CF$_3$; $R^6$ and $R^{13}$ independently are N or CH; $R^7$ and $R^{14}$ independently are N or C; and $R^{15}$ is NO$_2$, COO, CN, CS$_2$, CFH$_2$, CF$_2$H, or CF$_3$. In some embodiments, $R^1$-$R^7$ are the same as $R^8$-$R^{14}$, respectively, i.e., $R^1$=$R^8$, $R^2$=$R^9$, and so on.

$R^1$, $R^2$, $R^8$, and $R^9$ independently are N, CH, C(OH), C(SH), C(CFH$_2$), C(CF$_2$H), or C(CF$_3$). In some embodiments, one of $R^1$ and $R^2$ is CH and the other of $R^1$ and $R^2$ is N, and one of $R^8$ and $R^9$ is CH and the other of $R^8$ and $R^9$ is N. In one embodiment, $R^2$ and $R^9$ are N, and $R^1$ and $R^8$ are CH. In an independent embodiment, $R^1$ and $R^8$ are N, and $R^2$ and $R^9$ are CH.

In any or all of the above embodiments, (i) one of $R^6$ and $R^7$ is N and the other of $R^6$ and $R^7$ is C or CH (as required to satisfy valence requirements), and (ii) one of $R^{13}$ and $R^{14}$ is N and the other of $R^{13}$ and $R^{14}$ is C or CH (as required to satisfy valence requirements). In one embodiment, $R^6$ and $R^{13}$ are N, $R^7$ and $R^{14}$ are C, and the bonds indicated with " --- " are double bonds. In an independent embodiment, $R^6$ and $R^{13}$ are CH, $R^7$ and $R^{14}$ are N, and the bonds indicated with " --- " are single bonds.

In one embodiment, $R^1$ and $R^8$ are CH; $R^7$ and $R^{14}$ are C; $R^2$, $R^6$, $R^9$, and $R^{13}$ are N; and the bonds indicated with " --- " are double bonds. In an independent embodiment, $R^1$, $R^7$, $R^8$, and $R^{14}$ are N; $R^2$, $R^6$, $R^9$, and $R^{13}$ are CH; and the bonds indicated with " --- " are single bonds.

In any or all of the above embodiments, $R^5$ and $R^{12}$ independently are NH, NCH$_3$, O, S, CH$_2$, C(H)OH, C(H)SH, C(H)CFH$_2$, C(H)CF$_2$H, or C(H)CF$_3$. In one embodiment, $R^5$ and $R^{12}$ independently are NH, NCH$_3$, O, or S. In an independent embodiment, $R^5$ and $R^{12}$ independently are NH, O, or S. In another independent embodiment, $R^5$ and $R^{12}$ are NH.

In any or all of the above embodiments, $R^3$ and $R^{10}$ independently are Br, F, Cl, OH, SH, NH$_2$, NO$_2$, CH$_3$, CFH$_2$, CF$_2$H, or CF$_3$. In one embodiment, $R^3$ and $R^{10}$ independently are Br, F, Cl, OH, or SH. In an independent embodiment, $R^3$ and $R^{10}$ independently are Br, F, or Cl. In another independent embodiment, $R^3$ and $R^{10}$ are Br.

In any or all of the above embodiments, $R^4$ and $R^{11}$ independently are C=O, C=S, C(H)CFH$_2$, C(H)CF$_2$H, C(H)CF$_3$, SO$_2$, or SO. In one embodiment, $R^4$ and $R^{11}$ independently are C=O, C=S, C(H)CFH$_2$, C(H)CF$_2$H, or C(H)CF$_3$. In an independent embodiment, $R^4$ and $R^{11}$ independently are C=O or C=S. In another independent embodiment, $R^4$ and $R^{11}$ are C=O.

In any or all of the above embodiments, $R^{15}$ is NO$_2$, COO, CN, CS$_2$, CFH$_2$, CF$_2$H, or CF$_3$. In one embodiment, $R^{15}$ is NO$_2$, COO, CFH$_2$, CF$_2$H, or CF$_3$. In an independent embodiment, $R^{15}$ is NO$_2$ or COO. In another independent embodiment, $R^{15}$ is NO$_2$.

In any or all of the above embodiments, $R^{16}$ is N, CH, C(OH), C(SH), C(CFH$_2$), C(CF$_2$H), or C(CF$_3$), and $R^{17}$ is NH, NCH$_3$, O, S, CH$_2$, C(H)OH, C(H)SH, C(H)CFH$_2$, C(H)CF$_2$H, or C(H)CF$_3$. In one embodiment, $R^{16}$ is N, CH, C(OH), C(CFH$_2$), C(CF$_2$H), or C(CF$_3$), and $R^{17}$ is NH, NCH$_3$, O, S, CH$_2$, or C(H)OH. In an independent embodiment, $R^{16}$ is N or CH and $R^{17}$ is NH or CH$_2$, wherein at least one of $R^{16}$ and $R^{17}$ includes nitrogen. In another independent embodiment, $R^{16}$ is N and $R^{17}$ is NH.

In certain embodiments, the compound is 3-bromo-6-[3-(bromo-2-oxo-1H-pyrazolo[1,5-a]pyrimidin-6-yl)-4-nitro-1H-pyrazol-5-yl]-1H-pyrazolo[1,5-a]pyrimidin-2-one, also referred to herein as "ANY1":

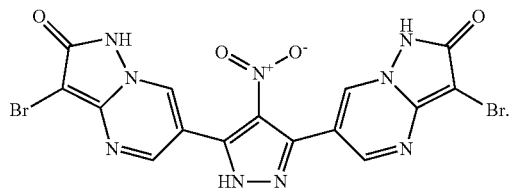 [SMILES: O=c1[nH]n2cc(-c3n[nH]c(-c4cnc5c(Br)c(=O)[nH]n5c4)c3[N+](=O)[O-])cnc2c1Br]

In an independent embodiment, the compound is 6,6'-(4-nitro-1H-pyrazole-3,5-diyl)bis(3-bromo-7-methylpyrazolo[1,5-a]pyrimidin-2(1H)-one), also referred to herein as "compound 8":

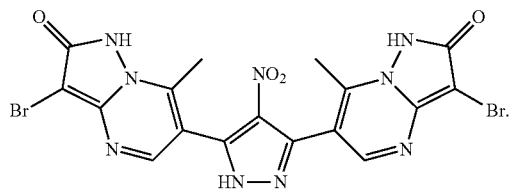 [SMILES: Cc1c(-c2n[nH]c(-c3cnc4c(Br)c(=O)[nH]n4c3C)c2[N+](=O)[O-])cnc2c(Br)c(=O)[nH]n12]

Compounds according to Formula A and/or Formula I can be synthesized by conventional methods known to synthetic organic chemists. A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the disclosed compounds encompass any tautomeric, conformational isomeric, optical isomeric, and/or geometric isomeric forms of the compounds described herein, as well as mixtures of these various different isomeric forms.

III. Pharmaceutical Compositions

Embodiments of the disclosed pharmaceutical compositions include a compound according to Formula A, or a stereoisomer, tautomer, or pharmaceutically acceptable salt thereof, and fosfomycin or a pharmaceutically acceptable salt thereof. In some embodiments, the pharmaceutical composition includes a compound according to Formula I, or a stereoisomer, tautomer, or pharmaceutically acceptable salt thereof, and fosfomycin or a pharmaceutically acceptable salt thereof. In one embodiment, the compound is 3-bromo-6-[3-(3-bromo-2-oxo-1H-pyrazolo[1,5-a]pyrimidin-6-yl)-4-nitro-1H-pyrazol-5-yl]-1H-pyrazolo[1,5-a]pyrimidin-2-one or 6,6'-(4-nitro-1H-pyrazole-3,5-diyl)bis(3-bromo-7-methylpyrazolo[1,5-a]pyrimidin-2(1H)-one). In an independent embodiment, the compound is 3-bromo-6-[3-(3-bromo-2-oxo-1H-pyrazolo[1,5-a]pyrimidin-6-yl)-4-nitro-1H-pyrazol-5-yl]-1H-pyrazolo[1,5-a]pyrimidin-2-one. Suitable salts of fosfomycin include, but are not limited to, fosfomycin tromethamine ([1,3-dihydroxy-2-(hydroxymethyl)propan-2-yl]azanium; hydroxy-[(2R,3S)-3-methyloxiran-2-yl]phosphinate) and fosfomycin disodium.

Embodiments of pharmaceutical compositions for administration to a subject can include at least one further pharmaceutically acceptable additive such as pharmaceutically acceptable carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The compounds and fosfomycin (hereinafter collectively referred to as "the agents") disclosed herein can be administered to subjects by a variety of mucosal administration modes, including by oral, rectal, intranasal, intrapulmonary, or transdermal delivery, or by topical delivery to other surfaces. Optionally, the agents can be administered by non-mucosal routes, including by intramuscular, subcutaneous, intravenous, intra-arterial, intra-articular, intraperitoneal, intrathecal, intracerebroventricular, or parenteral routes. In other alternative embodiments, the agents can be administered ex vivo by direct exposure to cells, tissues or organs originating from a subject.

To formulate the pharmaceutical compositions, the agents can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween® 80 polyethylene sorbitol ester or Miglyol® 812 triglycerides), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The agents can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The agents can be combined with the base or vehicle according to a variety of methods, and release of the agents can be by diffusion, disintegration of the vehicle, or associated formation of water channels. In some circumstances, the agent is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the agents can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-caprolactone-CO-lactic acid), poly(epsilon.-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the agent can be delivered to a subject in a manner consistent with conventional methodologies associated with management of the disorder for which treatment or prevention is sought. In accordance with the disclosure herein, a prophylactically or therapeutically effective amount of the agent is administered to a subject in need of such treatment for a time and under conditions sufficient to prevent, inhibit, and/or ameliorate a selected disease or condition or one or more symptom(s) thereof.

The administration of the agents can be for either prophylactic or therapeutic purpose. When provided prophylactically, the agents are provided in advance of any symptom. The prophylactic administration of the agents serves to prevent or ameliorate any subsequent disease process. When provided therapeutically, the agents are provided at (or shortly after) the onset of a symptom of disease or infection.

For prophylactic and therapeutic purposes, the agents can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosages of the agents can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosages of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the agent are outweighed in clinical terms by therapeutically beneficial effects. A non-limiting range for a therapeutically effective amount of an agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight. Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

IV. Methods of Use

The compounds according to Formula A and Formula I disclosed herein, including stereoisomers, tautomers, and pharmaceutically acceptable salts thereof, may be used in conjunction with fosfomycin or a pharmaceutically acceptable salt thereof for inhibiting growth of a fosfomycin-resistant bacterium, such as a fosfomycin-resistant bacterium that produces a FosA enzyme. In some embodiments, the fosfomycin-resistant bacterium is a Gram-negative bacterium. Exemplary Gram-negative bacteria include, but are not limited to *Enterobacter cloacae, Klebsiella pneumoniae, Pseudomonas aeruginosa*, and *Escherichia coli*.

A fosfomycin-resistant bacterium is contacted with (i) fosfomycin or a pharmaceutically acceptable salt thereof (hereinafter simply referred to as fosfomycin) and (ii) an effective amount of a compound according to Formula A or Formula I as disclosed herein, or a pharmaceutically acceptable salt thereof (hereinafter simply referred to as the compound). The fosfomycin-resistant bacterium may be contacted in vitro, in vivo, or ex vivo. In some embodiments, inhibiting the fosfomycin-resistant bacterium treats an infection caused by the bacterium.

The effective amount of the compound is an amount sufficient to inhibit growth of the fosfomycin-resistant bacterium (in combination with fosfomycin). In some embodiments, the compound has an $IC_{50}$ of less than 100 µM, less than 50 µM, less than 20 µM, or less than 10 µM. The compound may have an $IC_{50}$ of 1-100 µM, 5-50 µM, or 5-20 µM. Thus, the effective amount of the compound may be an amount sufficient to provide an in vitro or in vivo concentration within a range of 1-100 µM, 5-50 µM, or 5-20 µM. In certain embodiments, the effective amount is an amount sufficient to provide an in vivo concentration within a range of 5-20 µM.

Therapeutically effective amounts of fosfomycin are known to clinicians. In one embodiment, a therapeutically effective amount of fosfomycin for an adult human is 3 grams of fosfomycin (5.63 g of fosfomycin tromethamine) in a single oral dose. In another embodiment, fosfomycin disodium salt is administered intravenously at an adult human dose of 12-24 g in 2-4 divided doses (each dose is no more than 8 g), a child's dose (1-12 years, 10-40 kg body weight) of 200-400 mg/kg body weight in 3-4 divided doses, or an infant's dose (up to 10 kg body weight) of 200-300 mg/kg body weight in three divided doses.

Contacting the bacterium with the fosfomycin and the compound may comprise administering a therapeutically effective amount of fosfomycin and the effective amount of the compound or a pharmaceutically acceptable salt thereof to a subject identified as having, or being at risk of having, an infection caused by a fosfomycin-resistant bacterium. The subject may be a mammal such as a human or a non-human mammal. Administration of the therapeutically effective amount of fosfomycin and the effective amount of the compound may be performed simultaneously or sequentially in any order. Sequential administration may occur over a period ranging from a few seconds to a few hours, e.g., within a period of from less than one minute to three hours. In some embodiments, administering the therapeutically effective amount of fosfomycin and the effective amount of the compound comprises administering an amount of a pharmaceutical composition comprising the therapeutically effective amount of fosfomycin and the effective amount of the compound. In an independent embodiment, the method includes administering an amount of a first pharmaceutical composition comprising the therapeutically effective amount of fosfomycin and administering an amount of a second pharmaceutical composition comprising the effective amount of the compound.

In certain embodiments, the compound is 3-bromo-6-[3-(3-bromo-2-oxo-1H-pyrazolo[1,5-a]pyrimidin-6-yl)-4-nitro-1H-pyrazol-5-yl]-1H-pyrazolo[1,5-a]pyrimidin-2-one:

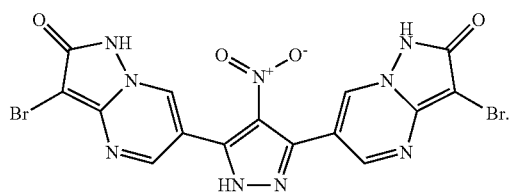 [SMILES: O=c1[nH]n2cc(-c3n[nH]c(-c4cnc5c(Br)c(=O)[nH]n5c4)c3[N+](=O)[O-])cnc2c1Br]

In such embodiments, the therapeutically effective amount may be an amount sufficient to provide an in vivo concentration within a range of from 5 µM to 20 µM.

In in independent embodiment, the compound is 6,6'-(4-nitro-1H-pyrazole-3,5-diyl)bis(3-bromo-7-methylpyrazolo[1,5-a]pyrimidin-2(1H)-one):

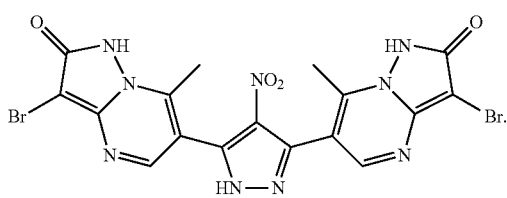

A therapeutically effective amount of a third agent may be co-administered with the fosfomycin and the compound. The third agent may be administered separately or together with the fosfomycin, the compound, or both the fosfomycin and the compound. The third agent may be administered by the same route or a different route. If administered concurrently, the fosfomycin, the compound, and the third agent may be combined into a single pharmaceutical composition or may be administered concurrently as two or three pharmaceutical compositions. The third agent may be, for example, an antibiotic, a fever reducer, an anti-inflammatory agent, or any other active agent suitable for ameliorating one or more signs or symptoms of the infection.

V. EXAMPLES

Example 1

FosA Screening Assay

A high-throughput screening (HTS) assay was developed to screen compounds for inhibition of the FosA enzyme. The enzyme facilitates glutathione-mediated nucleophilic attack on the fosfomycin to open the epoxide ring, rendering the drug inactive. A fluorescence-based assay utilizing monochlorobimane (mBCl) was developed and used to quantify the amount of glutathione consumed in the FosA reaction as shown in Scheme 2. The mBCl reacts with glutathione to produce a fluorescent adduct. The fluorescent adduct has $\lambda_{ex}$ of 390 nm, and a $\lambda_{em}$ of 478 nm. Diminishing fluorescence indicates glutathione consumption attributed to FosA activity, whereas steady-state fluorescence or a slower reduction in the fluorescence level indicates a lack or diminished rate of glutathione consumption when FosA activity is inhibited. The assay was adapted for use in a 96-well plate.

Scheme 2

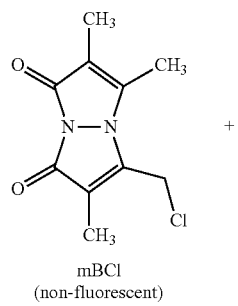

mBCl
(non-fluorescent)

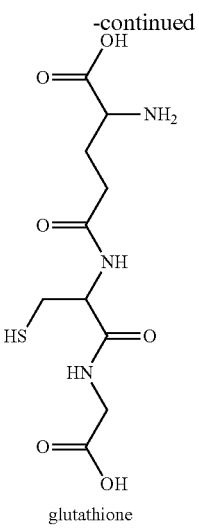

glutathione

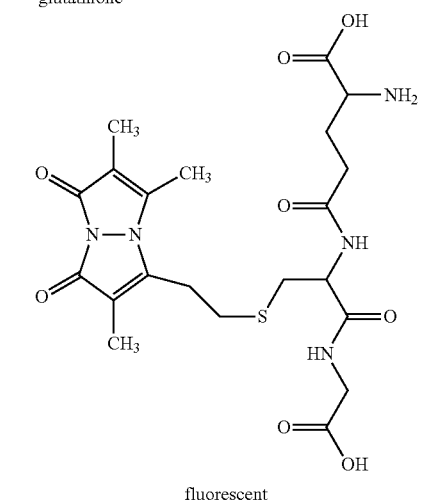

fluorescent

The TimTec ApexScreen compound library of 5040 compounds (TimTec LLC, Newark, Del.) was screened for potential FosA inhibitors. A solution of 125 nM FosA was prepared in 0.1 M sodium phosphate buffer pH 8 containing 50 μM $MnCl_2$ and 100 mM KCl. FosA$^{KP}$ (K. pneumoniae chromosomal FosA) was used. This solution was then incubated with varying concentrations of the compounds (0-60 μM) at room temperature for 10 minutes. Reactions were then initiated by the addition of 5 mM glutathione and 7 mM fosfomycin. Following a 45 minute reaction time, reactions were quenched with 3 reaction volumes of 100% chilled methanol. To quantify unconsumed glutathione, the reactions were diluted 40-fold in 0.1 M sodium phosphate buffer pH 8 containing 50 μM $MnCl_2$, 100 mM KCl, 1 mM EDTA and 0.5 mM monochlorobimane (mBCl). A glutathione standard curve with two-fold dilutions from 0-500 μM was also prepared. After 30 minutes of incubation with shaking, the plate was read at $\lambda_{ex}$ 390 nm; $\lambda_{em}$ 478 nm with $\lambda_{cutoff}$ 435 nm. The signal-to-background ratio was 4.02, with a signal window of 700, a signal-to-noise ratio of 8, a coefficient variation of 7.4%, and a Z' factor of 0.52. A linear regression was fit to the glutathione standard curve values, from which the glutathione remaining in each reaction was interpolated. The glutathione consumed was determined by subtracting the glutathione remaining in enzyme reactions from the glutathione remaining in the no enzyme control. These differences were used to calculate rates of reaction and percent reaction based on the uninhibited, no drug rates. This was plotted as the $\log_{10}$[compound (μm)] vs percent reaction and fit using a log(inhibitor) vs. normalized response regression (PRISM software, GraphPad Software, Inc., La Jolla, Calif.). FIG. 1 shows the activity of, one compound, ANY1 (3-bromo-6-[3-(3-bromo-2-oxo-1H-pyrazolo[1,5-a]pyrimidin-6-yl)-4-nitro-1H-pyrazol-5-yl]-1H-pyrazolo[1,5-a]pyrimidin-2-one), and several analogs of ANY1. ANY1 exhibited excellent inhibition of FosA with an $IC_{50}$ of 5 μM. A second compound, ANY2, had an $IC_{50}$ of 100 μM. Other screened compounds were ineffective with an $IC_{50}$>500 μM.

To evaluate the mechanism of action, steady-state experiments were carried out from varying concentrations of fosfomycin and 0, 5, 10 or 20 μM ANY1. Assays were carried out in a volume of 50 μl at 25° C. in 0.1 M sodium phosphate buffer (pH 8.0) containing 50 mM KCl, 25 μM $MnCl_2$, 30 mM glutathione, and 0-50 mM fosfomycin. A 100 nM concentration of FosA was used to initiate the reaction, which was quenched after 20 minutes for FosA. Reactions were quenched by the addition of 150 μl methanol. Quenched reactions were diluted in 100 μl of 0.1 M sodium phosphate buffer (pH 8.0) containing 1 mM EDTA. Following the addition of 500 μM monochlorobimane, the concentration of glutathione was established by fluorescence spectroscopy using a SpectraMax M2 plate reader (Molecular Devices). A standard curve was prepared using 0 to 750 μM glutathione. Data were fitted to Michaelis Menten equations using SigmaPlot (Systat Software Inc., San Jose, Calif.). The results are shown in FIG. 2 and summarized in Table 2. ANY1 acts as a competitive inhibitor with respect to fosfomycin binding to FosA and a non-competitive inhibitor with respect to glutathione ($K_i$=11.6 μM, data not shown).

TABLE 2

|  | 20 μM ANY1 | 10 μM ANY1 | 5 μM ANY1 | 0 μM ANY1 |
|---|---|---|---|---|
| $V_{max}$ | 154.6 | 107 | 118.2 | 135.9 |
| $K_m$ | 15.55 | 0.96 | 0.84 | 0.30 |

Figure 3:
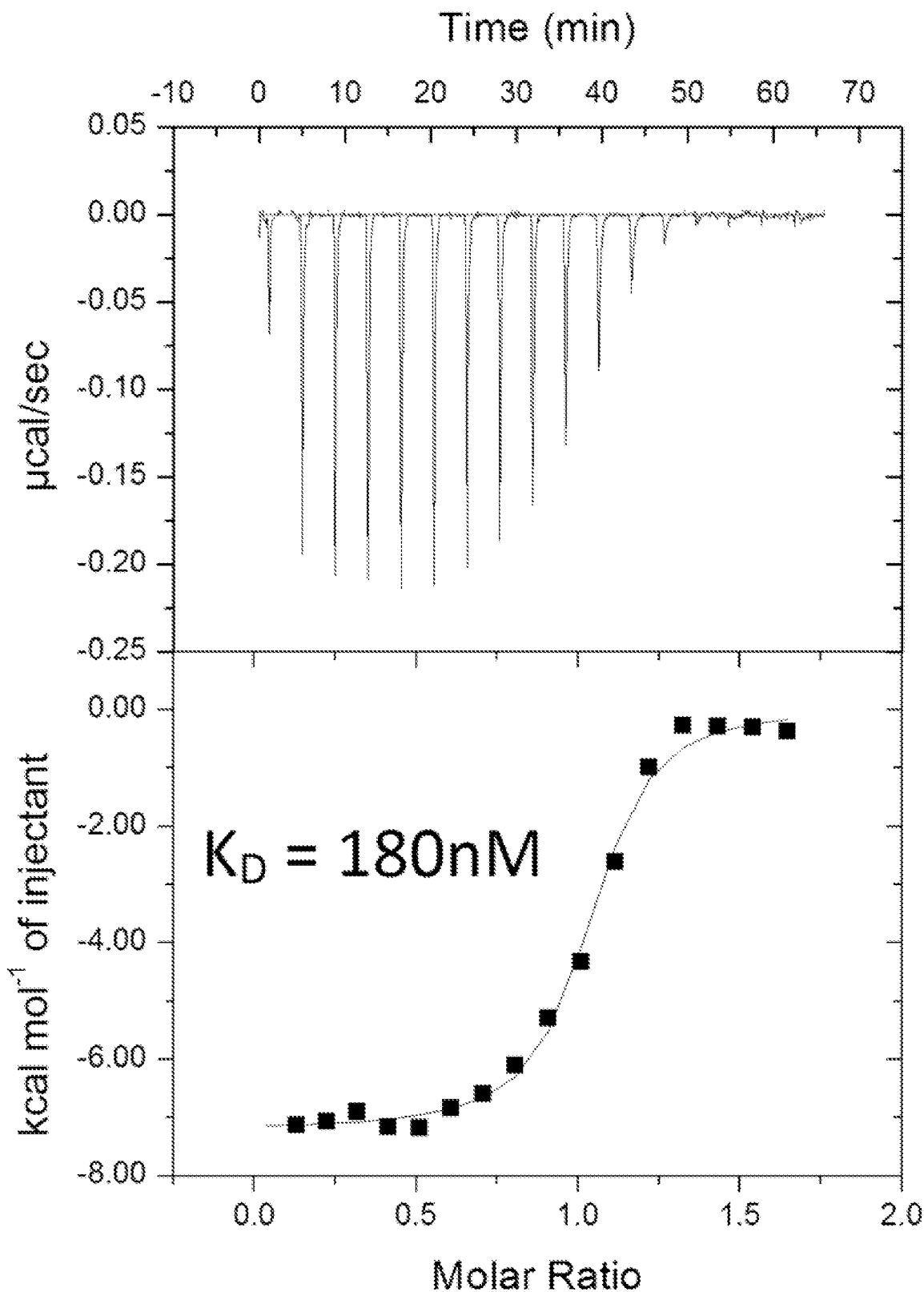
FIG. 3 shows the binding interaction between FosA$^{KP}$ and ANY1 assessed by isothermal calorimetry.

Isothermal titration calorimetry studies revealed that ANY1 binds to FosA$^{KP}$ (chromosomal *K. pneumoniae* FosA) with a $K_D$ of 180±30 nM and a stoichiometry of ~1:1 (ANY1:FosA$^{KP}$ monomer). FIG. 3 shows the binding interaction between FosA$^{KP}$ and ANY1. The studies also revealed that ANY1 did not bind to the related FosB enzyme from Gram-positive pathogens or to *E. coli* MurA (data not shown), thus highlighting ANY1 specificity for FosA.

Example 2

ANY1 Inhibition of Fosfomycin-Resistant Gram-Negative Bacteria

ANY1 was evaluated for its efficacy in inhibiting growth of several species of fosfomycin-resistant Gram-negative bacteria—*Enterobacter cloacae, Klebsiella pneumoniae, Pseudomonas aeruginosa*, and *Escherichia coli*. Each bacterial strain is resistant to fosfomycin and caries the species-specific fosfomycin-modifying gene encoding FosA.

An overnight culture of each antibiotic-resistant bacterium was grown in Mueller-Hinton Broth at 37° C., 150 rpm. The following day, the culture was diluted such that its $OD_{600}$ was 0.2. The diluted culture was allowed to grow at 37° C. for 1 h. Following this, the culture was diluted such that its $OD_{600}$ was 0.1. In a 96-well, round-bottom plate, three groups were set-up. Group one contained 32 μg/mL fosfomycin and 10 two-fold dilutions of ANY1. Group two contained 10 two-fold dilutions of ANY1 only. Group three contained 10 two-fold dilutions of fosfomycin (0-1024 μg/mL). All groups contained 25% volume of the 0.1 M culture and 25 μg/mL glucose-6-phosphate. The plate was incubated at 37° C. for up to 300 mM. The $OD_{600}$ was assessed every 30 mM. Data was analyzed in PRISM software or SigmaPlot® software (Systat Software Inc., San Jose, Calif.). The initial $OD_{600}$ subtracted as background, and fit with a logistic growth curve.

Figure 5A:
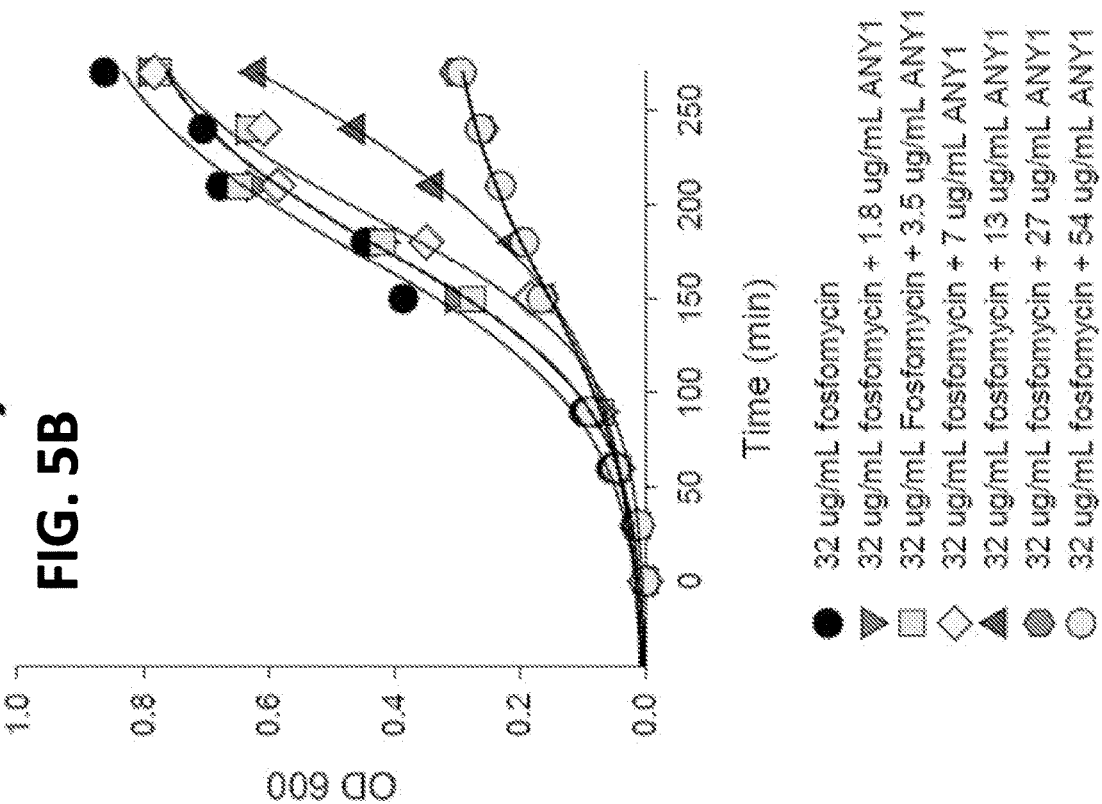
FIGS. 5A and 5B are graphs showing the inhibitory activity of ANY1 at various concentrations towards fosfomycin-resistant, FosA-producing *Klebsiella pneumoniae* in the absence (FIG. 5A) and presence (FIG. 5B) of 32 µg/mL fosfomycin.
Figure 5B:
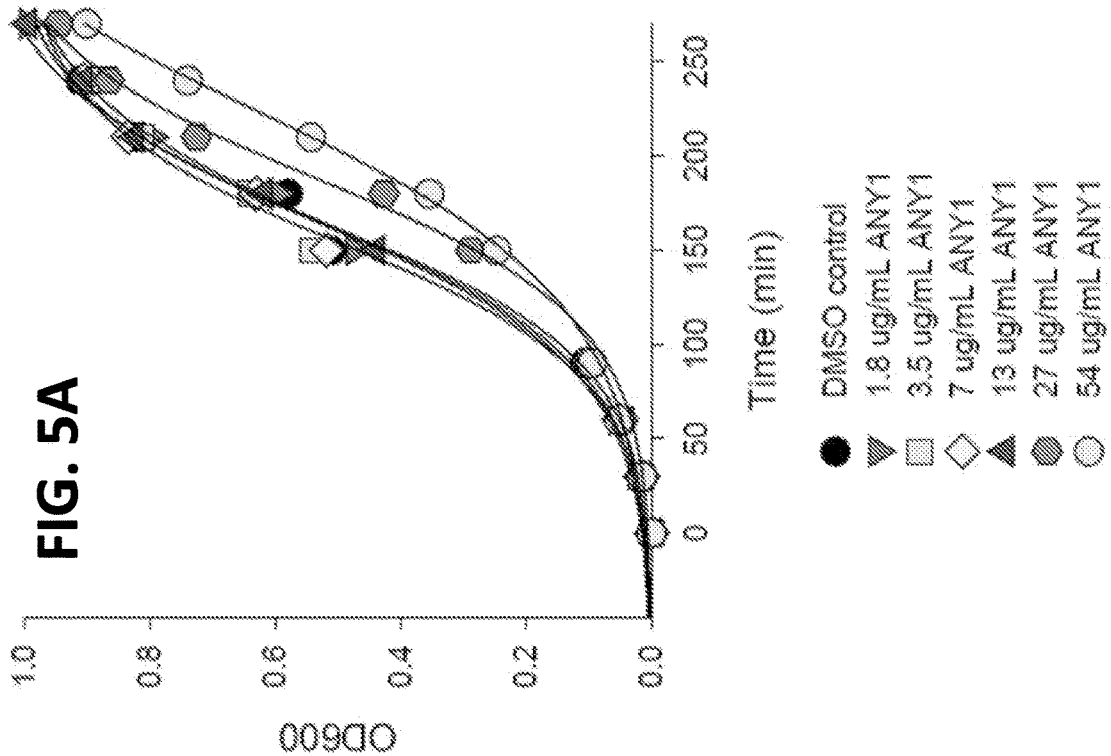

The results are shown in FIGS. 4-7: *Enterobacter cloacae*—FIGS. 4A-4B, *Klebsiella pneumoniae*—FIGS. 5A-5B, *Pseudomonas aeruginosa*—FIGS. 6A-6B, and *Escherichia coli*—FIGS. 7A-7B. ANY1 effectively inhibited FosA in each of the bacterial strains, thereby reversing fosfomycin resistance.

Figure 8B:
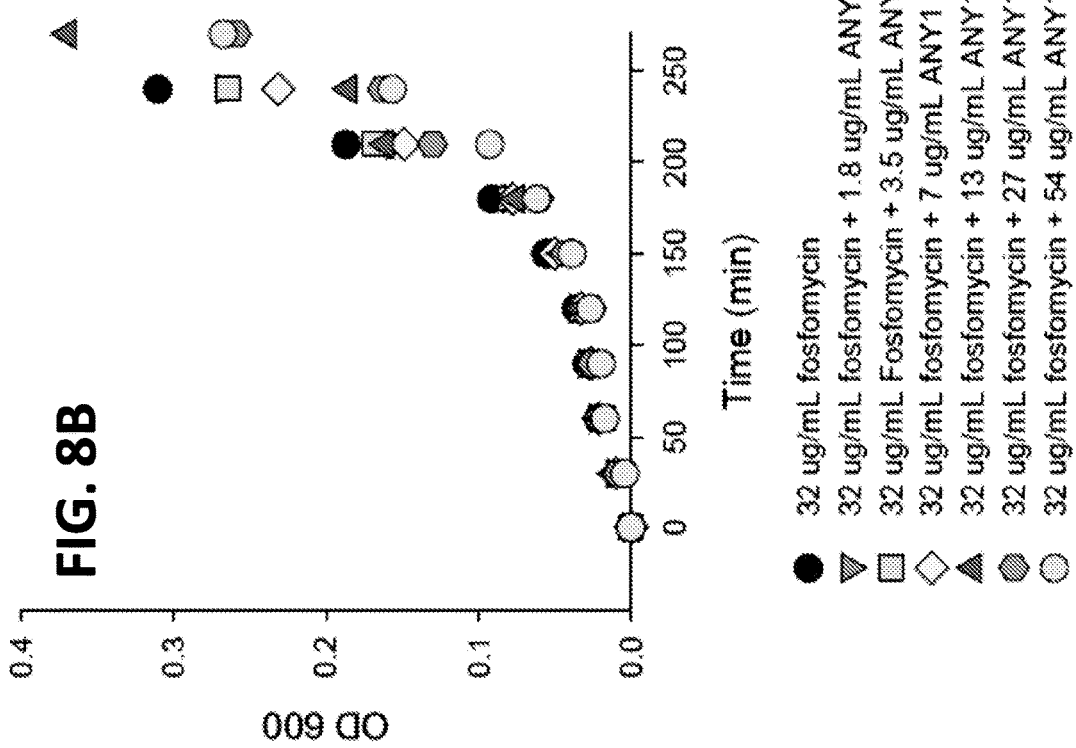
FIGS. 8A-8B are graphs showing the lack of inhibitory activity of ANY1 towards a fosfomycin-resistant, FosA-non-producing *Escherichia coli* strain containing a defective fosfomycin transporter uhpT in the absence (FIG. 8A) and presence (FIG. 8B) of 32 μg/mL, fosfomycin.
Figure 8A:
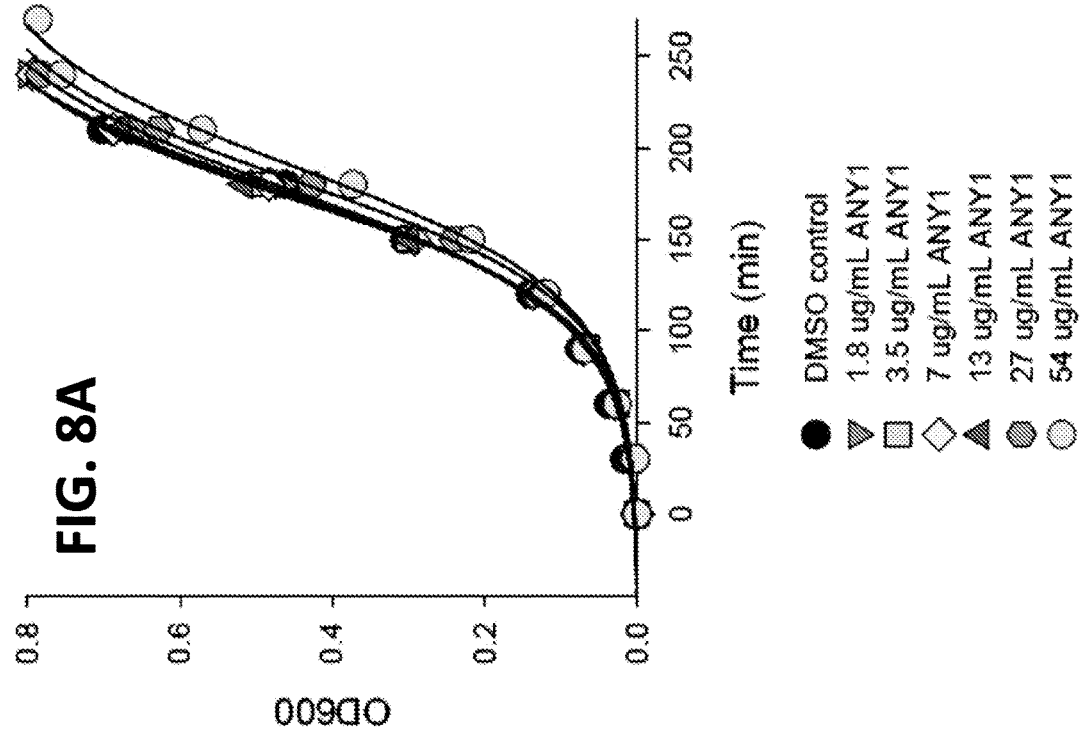

FIGS. 8A-8B show the growth curves of a fosfomycin-resistant *Escherichia coli* strain containing a deletion in the uhpT gene. This strain does not harbor the FosA gene. Fosfomycin resistance is conferred by decreased transport of the antibiotic across the bacterial cell wall. Consistent with its mechanism of action, ANY1 did not inhibit the bacterial growth.

Example 3

Crystal Structure of FosA$^{KP}$ in Complex with ANY1

The atomic resolution structures of FosA$^{KP}$ (1.2 Å resolution), FosA$^{KP}$-FOM (1.6 Å resolution), FosA$^{KP}$-ANY1 (3.1 Å resolution), FosA3 (2.7 Å resolution) and FosA3-ANY1 (3.5 Å resolution) were solved (Klontz et al., *Antimicrob Agents Chemother* Oct. 24, 2017, 61(11), pii: e01572-17).

Protein expression and purification for crystallization: FosA3 and FosA$^{KP}$ were cloned into the pET-22(b+) vector (Novagen) with the inclusion of a C-terminal His$_6$ tag, as described above. Both constructs were expressed in 6 liters of LB medium overnight at 18° C. in *E. coli* BL21(DE3)/pLysS cells after induction with 0.5 mM isopropyl-[3-D-thiogalactopyranoside (IPTG) at an $OD_{600}$ of 0.6. Cells were harvested by centrifugation (5,000×g for 15 mm) and lysed in PBS by sonication. The soluble fraction was purified using HisPur nickel-nitrilotriacetic acid (Ni-NTA) resin (Thermo Scientific) using a gradient of 10 to 500 mM imidazole. The protein was then dialyzed into 150 mM NaCl–50 mM Tris (pH 7.5) and then further purified by size exclusion chromatography (Superdex® 200 10/300 GL gel filtration column; GE Healthcare). It was then buffer exchanged into 75 mM NaCl–10 mM Tris, (pH 7.5) and concentrated.

Protein crystallization. For FosA3, protein was concentrated to 9 mg/ml and combined with 6 mM fosfomycin and 6 mM $MnCl_2$. The solution was centrifuged (19,150×g for 5 min), and 250 nl of the supernatant was combined with 250 nl of mother liquor (7% [vol/vol] ethylene glycol, 7% [wt/vol] polyethylene glycol 6000 [PEG 6000], 0.1 M HEPES [pH 6.95]) in sitting drops. For fosfomycin-bound FosA$^{KP}$, protein was concentrated to 9 mg/ml, combined with 6 mM fosfomycin disodium salt (Sigma-Aldrich; purity as determined by thin-layer chromatography [TLC], >98%) and 6 mM $MnCl_2$, and centrifuged (19,150×g for 5 min). One microliter of supernatant was combined in hanging drops with 1 μl of mother liquor (0.22 M KBr, 20% [wt/vol]

PEG 2000 monomethyl ether). For fosfomycin-unbound FosA$^{KP}$, protein was concentrated to 13 mg/ml and 1 μl of protein was combined in hanging drops with 1 μl of mother liquor (0.25 M MgCl$_2$, 20% [wt/vol] PEG 3350, 0.1 M bis-Tris [pH 5.5]). Resulting crystals were improved by streak seeding. Crystals were harvested and flash-cooled with liquid nitrogen in mother liquor supplemented with 20% (vol/vol) glycerol as a cryoprotectant.

X-ray diffraction, data processing, structure determination, and refinement. X-ray diffraction data for FosA3 and fosfomycin-bound FosA$^{KP}$ were collected using a Dectris 6M PILATUS detector (Dectris AG, Baden, Switzerland) on beamline 23-ID-D at the Advanced Photon Source (APS), processed using XDS (Kabsch, *Acta Crystallogr D Biol Crystallogr* 2010, 66:125-132), and scaled in AIMLESS (Evans, *Acta Crystallogr D Biol Crystallogr* 2013, 69:1204-1214; Winn et al., *Acta Crystallogr D Biol Crystallogr* 2011, 67:235-242). Both data sets were phased by molecular replacement in PHENIX using Phaser-MR (McCoy et al., *J Appl Crystallogr* 2007, 40:658-674) with PDB accession code 1LQP as a search model and further built and refined using Coot (Emsley et al., *Acta Crystallogr D Biol Crystallogr* 2004, 60:2126-2132) and PHENIX (Adams et al., *Acta Crystallogr D Biol Crystallogr* 2010, 66:213-221), respectively. Data for fosfomycin-unbound FosA$^{KP}$ was collected on beamline 23-ID-B at APS and processed as described above, except for fosfomycin-bound FosA$^{KP}$ as the search model for molecular replacement.

Accession number(s). The atomic coordinates have been deposited in the Protein Data Bank with codes 5V91, 5V3D, and 5VB0.

Figure 10A:
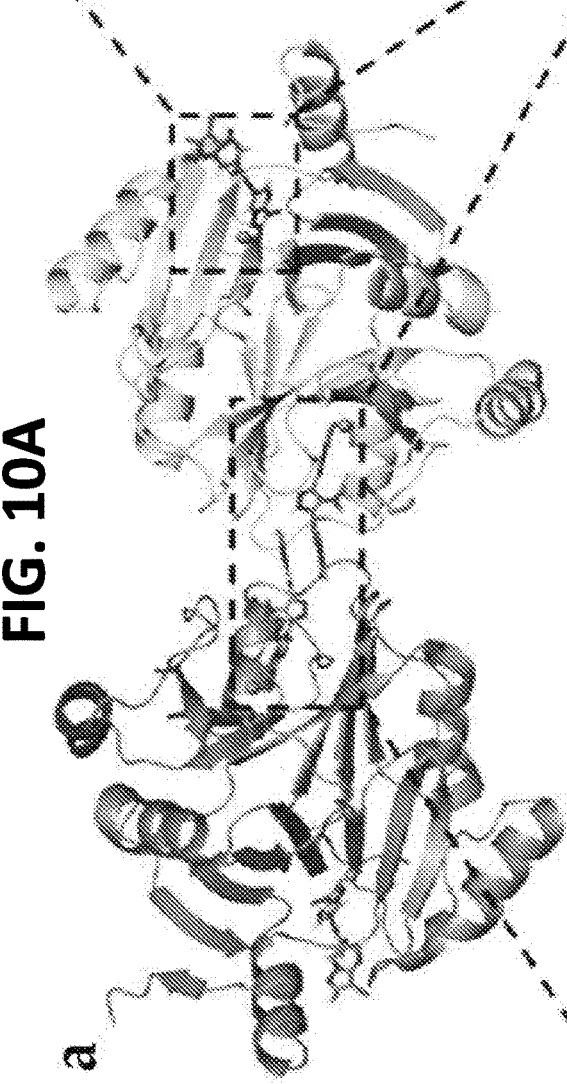
FIGS. 10A-10D show the crystal structure of FosA$^{KP}$ in complex with ANY1.
Figure 10B:
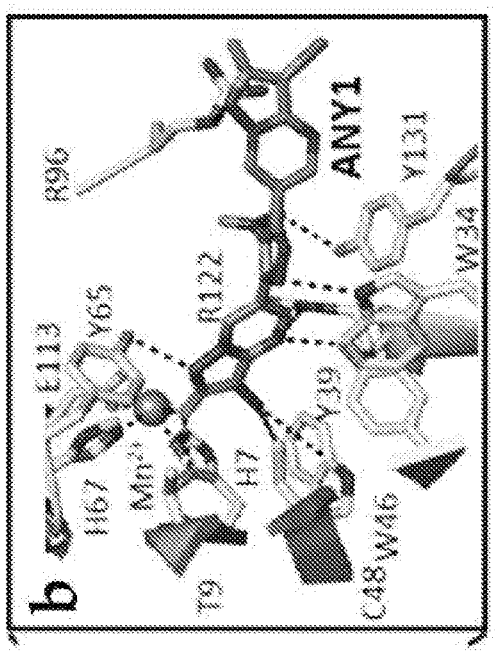
Figure 10C:
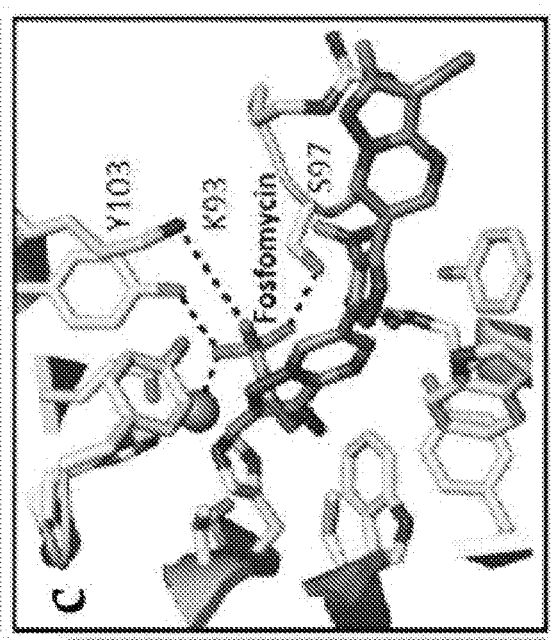
Figure 10D:
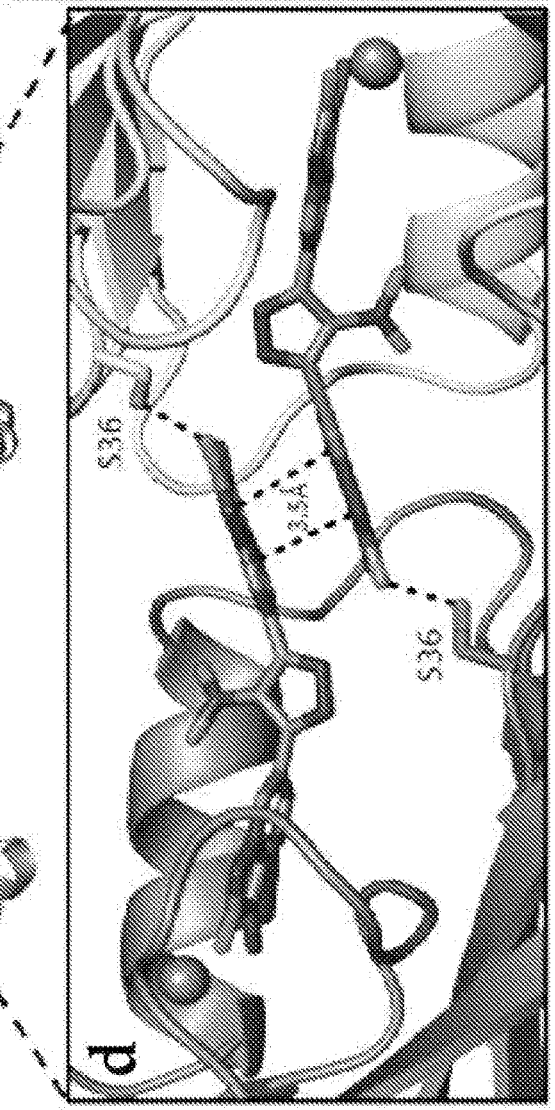

The data collection and refinement statistics for unliganded (or apo) FosA3, apo FosA$^{KP}$, and FosA$^{KP}$ in complex with fosfomycin (holo FosA$^{KP}$) are shown in FIG. 9. The FosA$^{KP}$ and FosA3 structures exhibit remarkable similarity to the related published structures of *P. aeruginosa* FosA (Rife et al., *J Am Chem Soc* 2002, 124(37)11001-3), and contain 2 active sites/dimer (1/monomer). ANY1 was found to bind at both active sites in FosA$^{KP}$ (FIG. 10A) and FosA3 (data not shown), where it makes contacts with multiple residues in the FosA$^{KP}$ active site (FIG. 10B). Consistent with the finding that ANY1 is a competitive inhibitor with respect to FOM, the ANY1 and FOM binding sites in FosA$^{KP}$ overlap (FIG. 10C). Drug-drug and drug-protein interactions between two adjacent FosA$^{KP}$ molecules (FIG. 10D).

Figure 12:
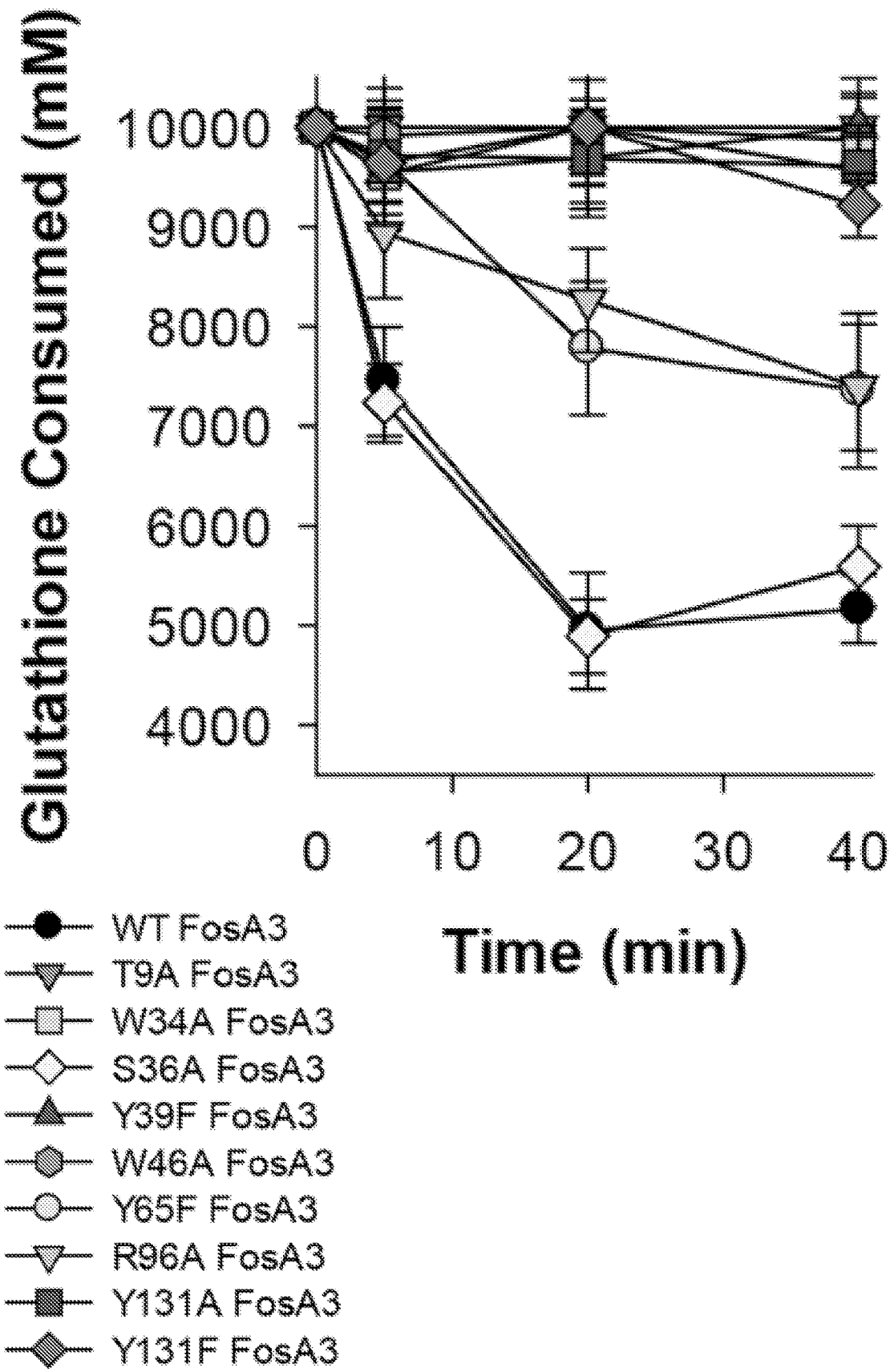
FIG. 12 is a graph showing the enzyme activity of FosA3 enzymes containing alanine or phenylalanine substitutions in the ANY1 binding site.

Sequence alignment of the residues involved in ANY1 binding reveal that they are highly conserved across FosA enzymes from different Gram-negative species (FIG. 11). This suggests: (i) that ANY1 should bind to and inhibit FosA from different Gram-negative bacteria; and (ii) that the genetic barrier to ANY1 resistance is expected to be high given that it interacts with conserved residues in the FosA active site. Introduction of alanine (positions 9, 34, 36, 46, 96 and 131) or phenylalanine (positions 39, 65 and 131) substitutions at key residues in the FosA3-ANY1 binding site either eliminated or significantly diminished enzyme activity FIG. 12. Tryptophan fluorescence binding studies confirmed the contribution of residues T9, W34, S36, W46 and Y131A in FosA3 to ANY1 binding (Table 4).

TABLE 4

| FosA3 Protein | $K_d$ (nM) | Fold-Change in $K_d$ (vs WT) |
|---|---|---|
| WT | 440.6 ± 50.1 | — |
| T9A | 1575.3 ± 97.6 | 3.6 (p < 0.05) |
| W34A | 2623.8 ± 204.6 | 6.0 (p < 0.05) |
| S36A | 1357.4 ± 132.5 | 3.1 (p < 0.05) |
| Y39F | 867.7 ± 200.7 | 2.0 |
| W46A | 2474.7 ± 111.0 | 5.6 (p < 0.05) |
| Y65F | 783.6 ± 74.7 | 1.8 |
| R96A | 540.8 ± 90.1 | 1.2 |
| Y131A | 4882 ± 770.0 | 11.1 (p < 0.05) |
| Y131F | 550.8 ± 28.0 | 1.3 |

Example 4

Antibacterial Activity of ANY1 Alone and in Combination with Fosfomycin

Figure 13A:
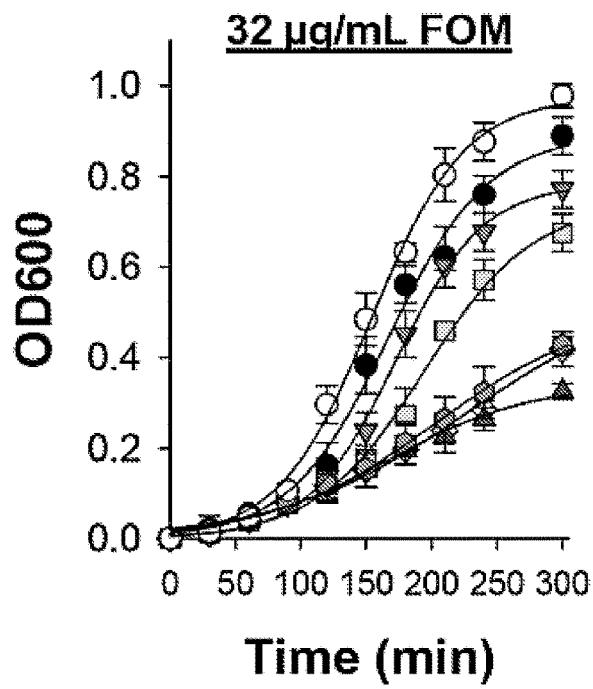
FIGS. 13A-13C are graphs showing growth curves of *K. pneumoniae* I1 in the presence of 32 μg/mL (13A), 64 μg/mL (13B), or 128 μg/mL (13C) fosfomycin and varying concentrations of ANY1.
Figure 13B:
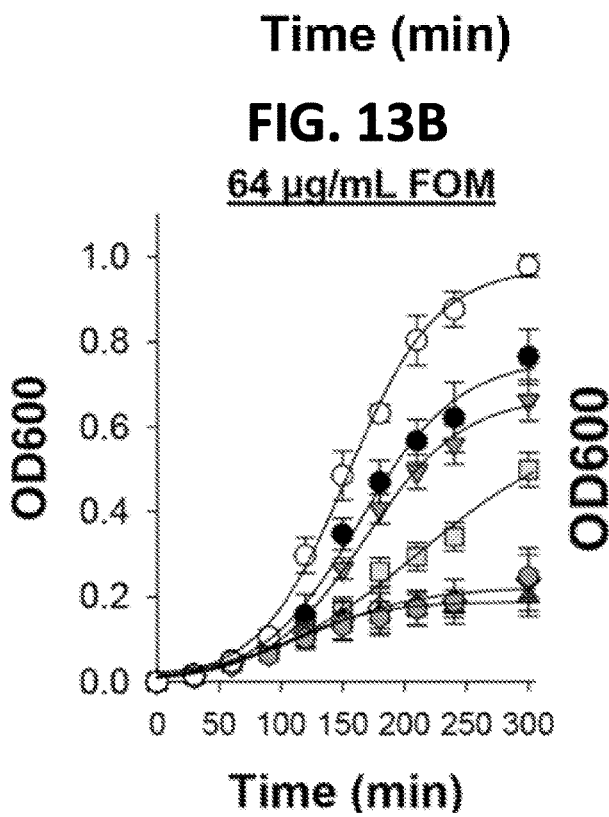
Figure 13C:
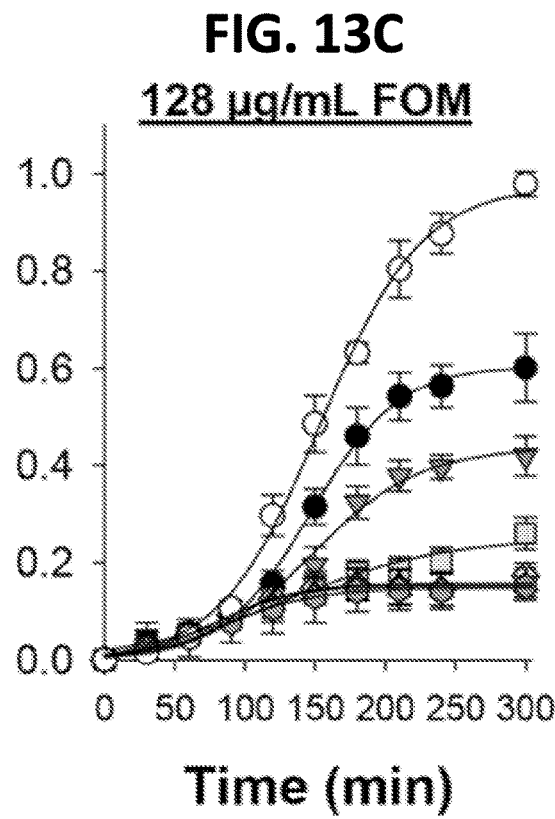

The antimicrobial activity of ANY1 against the carbapenemase (KPC)-producing *K. pneumoniae* clinical strain I1 was evaluated in the absence and presence of FOM (32, 64 and 128 μg/mL) by bacterial growth curve analysis. Briefly, an overnight culture of *K. pneumoniae* I1 was diluted in Mueller-Hinton broth in a 96-well plate, incubated at 37° C. (150 rpm), and OD$_{600}$ was assessed every 30 min. Bacterial growth was significantly attenuated when FOM was combined with ANY1, in a dose dependent manner FIGS. 13A-13C show the results obtained with 32, 64, and 128 μg/mL FOM, respectively, combined with ANY1 in doses from 14-224 μg/mL. The control (○) was *K. pneumoniae* I1 grown in the absence of FOM and ANY1.

Figure 14:
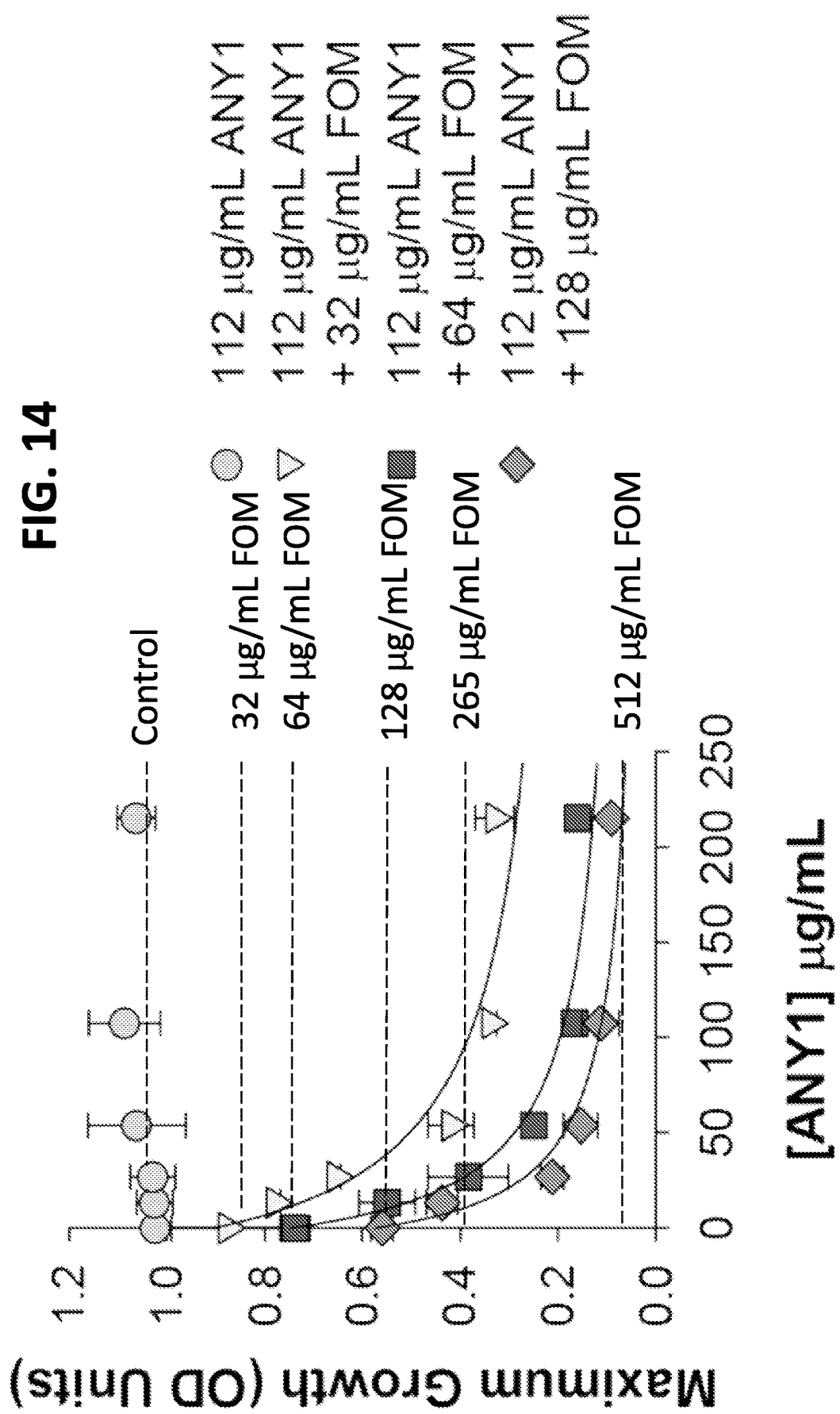
FIG. 14 is a graph showing the impact of fosfomycin (lines), ANY1 (circles), and combinations of fosfomycin+ANY1 on the maximum growth of *K. pneumoniae* I1.

The growth curves were modeled using a modified 3-parameter Gompertz equation (Zwietering et al., *Appl Environ Microbiol* 1990, 56(6)1875-81), which facilitated quantification of the lag time (min), growth rate (OD units/min) and maximum growth (OD units). FIG. 14 illustrates how FOM (lines), ANY1 (circles), and combinations of FOM+ANY1 impact the maximum growth of *K. pneumoniae* I1. The maximum growth value was determined from the curves in FIGS. 12A-12C using a 3-parameter Gompertz equation. ANY1 alone had no effect on the growth of *K. pneumoniae* I1, a finding which is consistent with the inhibitor's mechanism of action. However, it potentiated FOM activity in a dose dependent manner, resulting in ~6-fold increase in activity at the highest concentration tested.

Figure 15A:
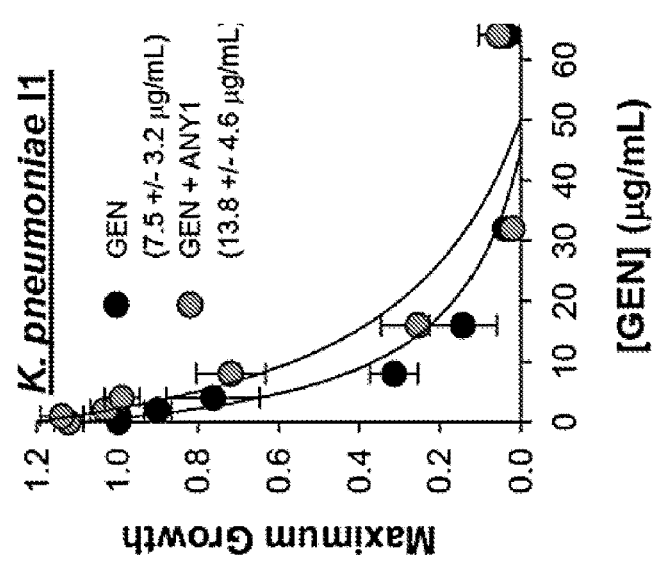
FIGS. 15A-15C show a fosfomycin-dose response curve for *K. pneumoniae* I1 (15A), a time-kill analysis for *K. pneumoniae* I1 (15B), and a gentamicin (GEN)±ANY1 dose-response curve for *K. pneumoniae* I1 (15C).
Figure 15B:
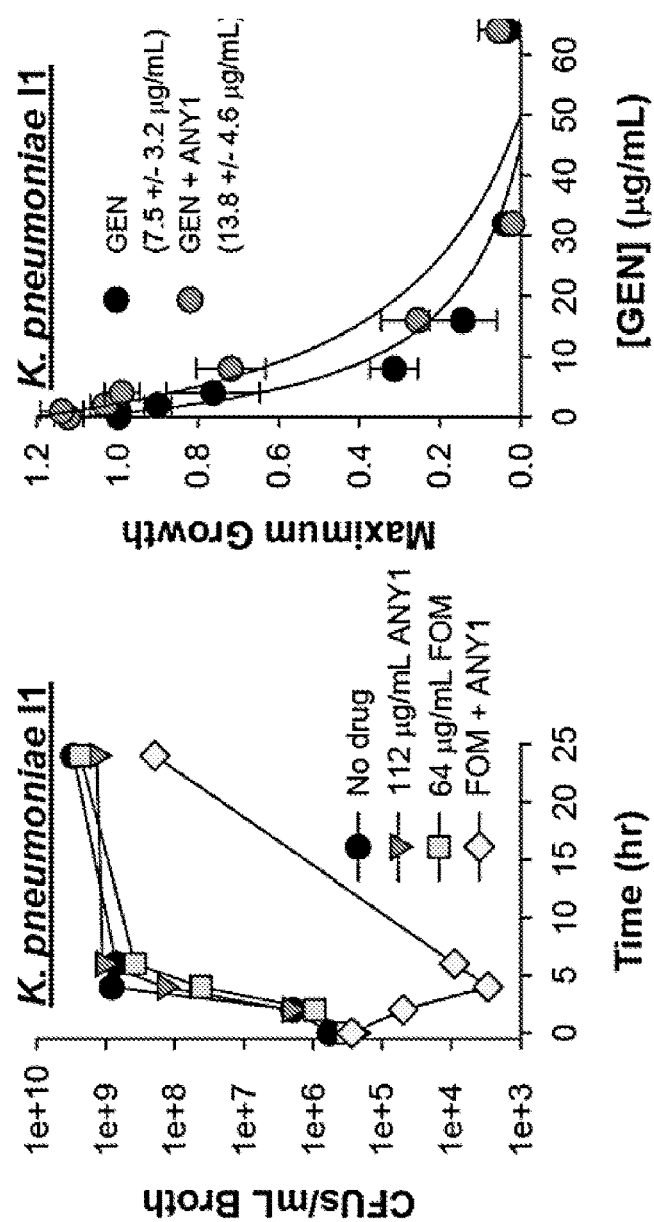
Figure 15C:
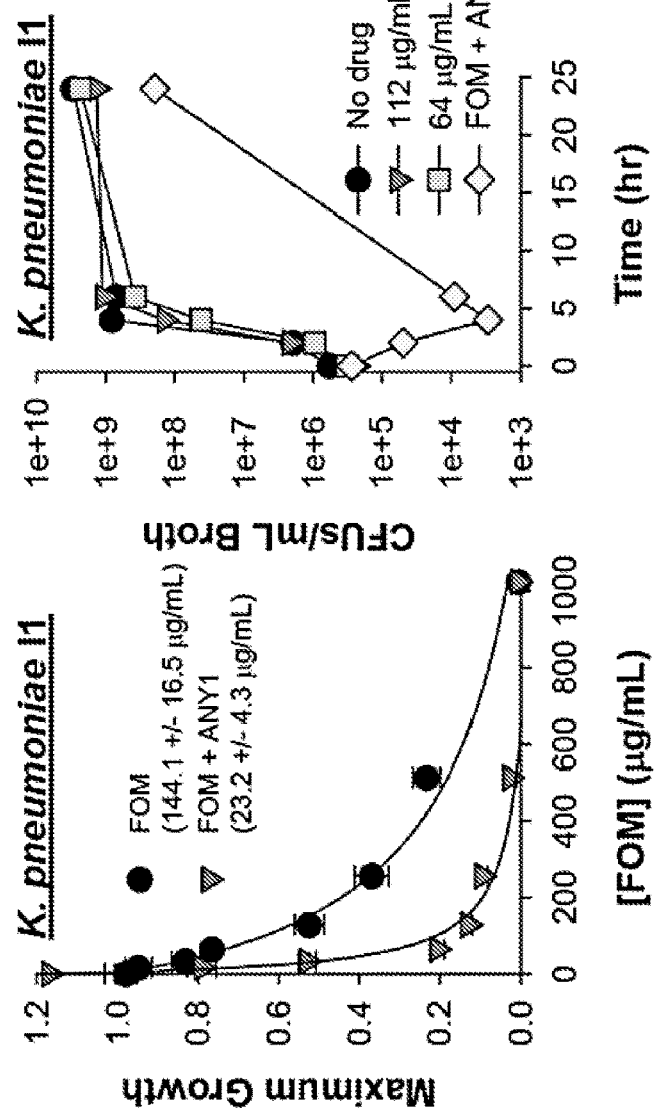
Figure 16C:
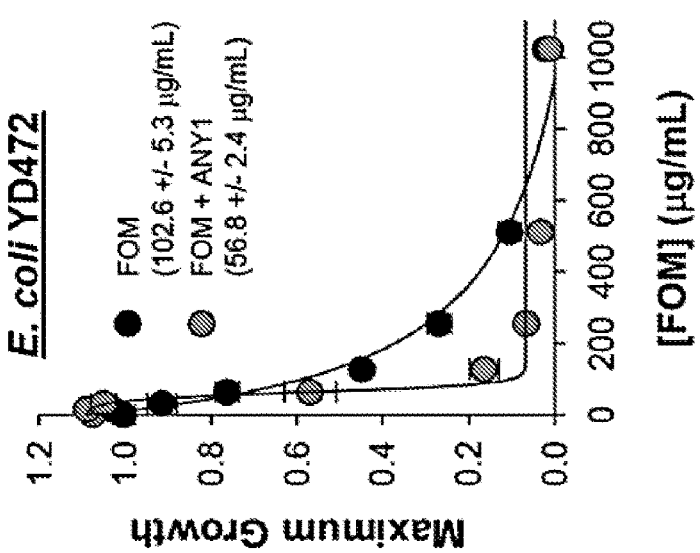
FIGS. 16A-16C show fosfomycin±ANY1 dose response curves for *E. cloacae* YD612 (16A), *S. marcescens* YDC760-2 (16B), and *E. coli* YD472 (16C).
Figure 16B:
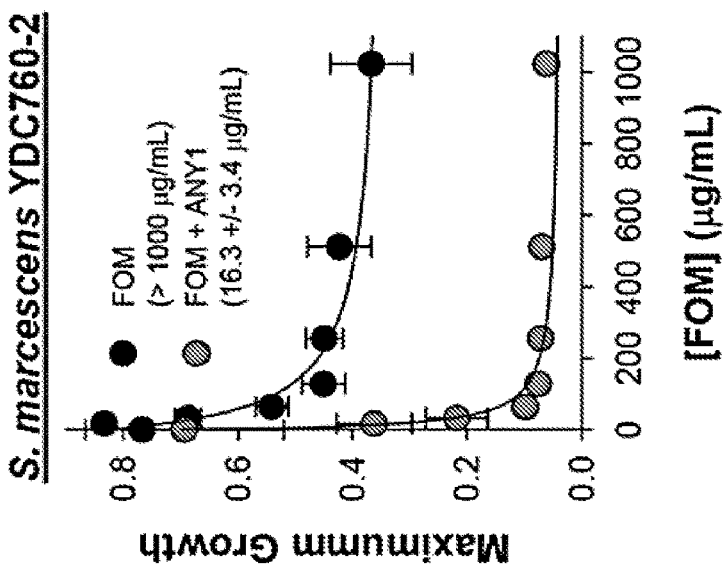
Figure 16A:
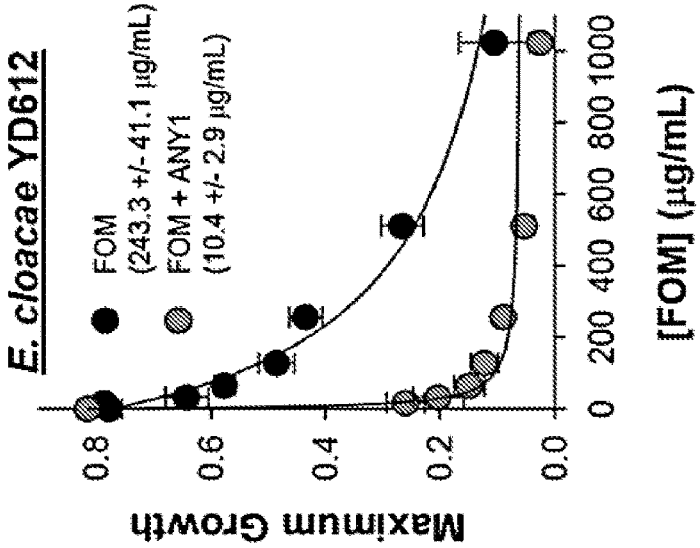

The effect of a single, high concentration of ANY1 (112 μg/mL) on FOM activity against *K. pneumoniae* I1 was evaluated using growth curve analysis as described above. The results are shown in FIG. 15A. ANY1 reduced the concentration of FOM required to decrease *K. pneumoniae* maximum growth by 50% (i.e. IC$_{50}$) ~6-fold (P<0.05): the IC$_{50}$ values for FOM were 144.1±16.5 μg/mL and 23.2±4.3 μg/mL in the absence and presence of ANY1, respectively. Time-kill experiments confirmed that ANY1 significantly increased FOM activity (FIG. 15B). In contrast to FOM, ANY1 did not alter the activity of gentamicin (FIG. 15C). Importantly, 112 μg/mL of ANY1 also significantly decreased the IC$_{50}$ for FOM for the KPC-producing clinical strains *E. cloacae* YDC612 (23-fold; P<0.05; FIG. 16A), *S. marcescens* YDC760-2 (>100-fold; P<0.05; FIG. 16B) and FosA3-producing *E. coli* YD472 (1.8-fold; P=0.04; FIG. 16C). The weaker effect of ANY1 in the *E. coli* clinical strain may be due to FosA expression levels resulting from plasmid-mediated expression in *E. coli* versus chromosomal FosA-expression in *K. pneumoniae, E. cloacae* and *S. marcescens*.

To evaluate potential cellular toxicity, the effect of varying concentrations of ANY1 (0-224 μg/mL) was assessed on the viability of human peripheral blood mononuclear cells, HK2 cells, which are a human-derived kidney epithelial cell line, and OK cells, which are a marsupial-derived cell line used to model proximal tubule epithelial cells of the kidney. In all cases, cell viability was assessed using the CellTiter-Glo® luminescent cell viability assay. ANY1 had no impact on cell viability in any of the cells tested (data not shown).

Example 5

Synthesis of Analogues

Figure 17:
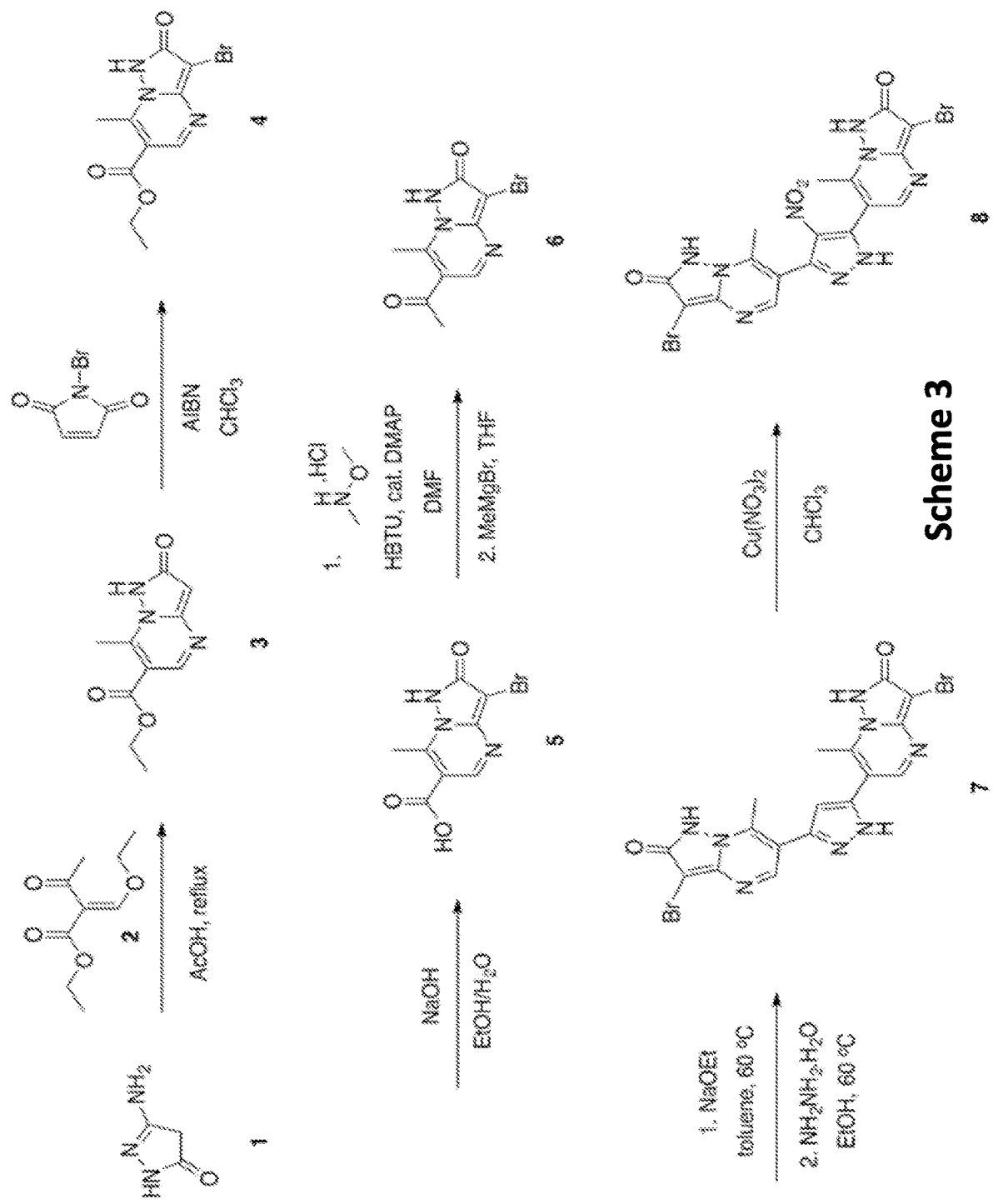
FIG. 17 is a synthetic scheme for preparing 6,6'-(4-nitro-1H-pyrazole-3,5-diyl)bis(3-bromo-7-methylpyrazolo[1,5-a]pyrimidin-2(1H)-one) (compound 8).

Scheme 3 (FIG. 17) is one synthetic pathway for preparing 6,6'-(4-nitro-1H-pyrazole-3,5-diyl)bis(3-bromo-7-methylpyrazolo[1,5-a]pyrimidin-2(1H)-one) (compound 8). Compound 8 differs from ANY1 by introduction of two additional methyl groups. Based on the crystal structure data, the methyl groups should be readily accommodated and may increase binding affinity. Briefly, pyrazol-3-one 1 is condensed with 2 to generate bicyclic 1,2-dihydropyrazolo[1,5-a]pyrimidine 3. Selective bromination of 3 can be accomplished under free radical (shown) or direct bromination conditions to furnish 4. At this stage, a portion of ester 4 will undergo saponification to generate acid 5.

Next, 5 is coupled to $CH_3NHOCH_3$ to yield the corresponding Weinreb amide, which can then be transformed to the corresponding methyl ketone 6 by reaction with the Grignard reagent methyl magnesium bromide. Ester 4 and methyl ketone 6 are then coupled to yield a 1,3-dicarbonyl compound that is condensed with hydrazine to yield the pyrazole core in compound 7. Finally, mild nitration with copper (II) nitrate will deliver compound 8, a direct analogue of ANY1.

Figure 18:
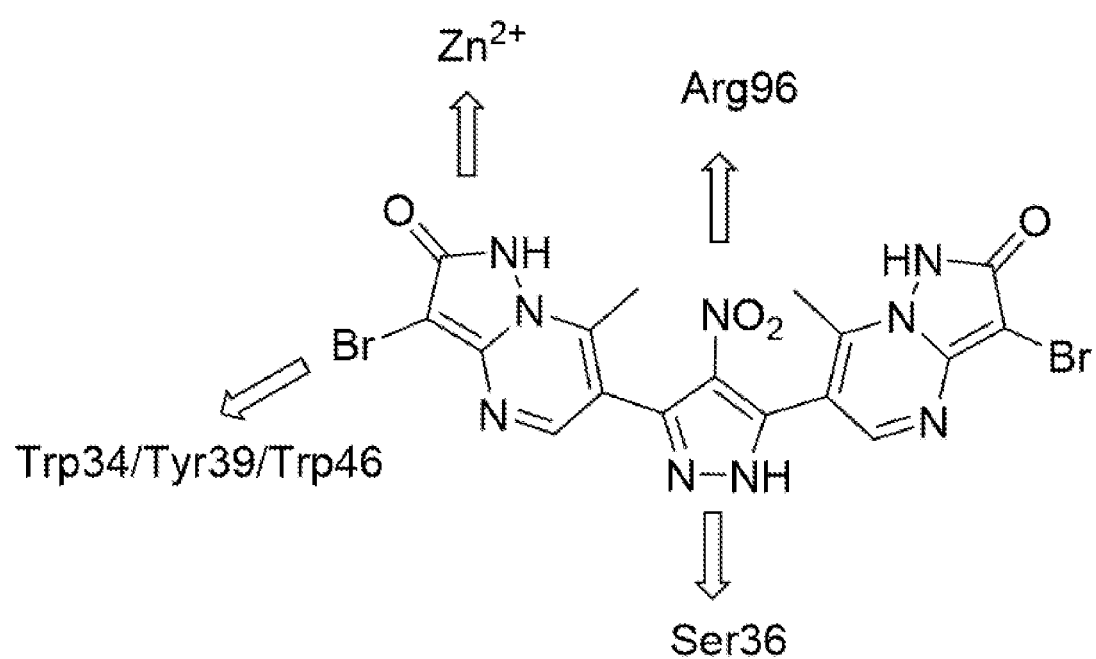
FIG. 18 shows sites of further modification to produce analogues of compound 8.

Based on the crystal structure of ANY1, additional modifications can be made to enhance binding to FosA as shown in FIG. 18. Putative biosteres, e.g., COOH, $SO_2CF_3$, can be introduced at the Arg96 binding site. Alternative and larger hydrophobic groups, e.g., Cl, phenyl, alkyl, can be introduced at the Trp34/Tyr39/Trp46 binding site. At the Ser36 site, alternative linkers that retain capacity for hydrogen bonding can be introduced, such as:

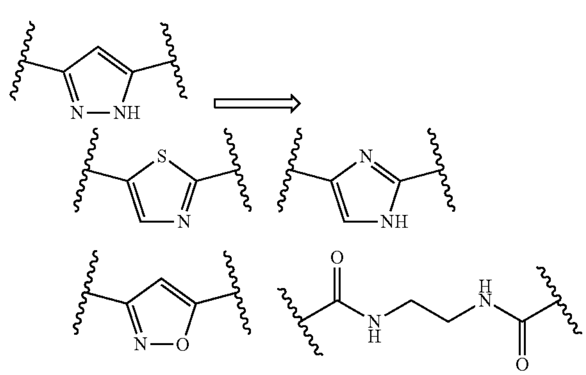

To simplify the synthetic chemistry and to expedite compound synthesis, identical modifications can initially be made to both 1,2-dihydropyrazolo[1,5-a]pyrimidine moieties. Once sufficient data is acquired with symmetrical derivatives of 8, a variety of acids 5 can then be coupled to a variety of methyl ketones 6 to give a range of unsymmetrical analogues, a goal that is readily facilitated by the short and modular synthesis. Based on the crystal structure of ANY1, the bromine fits comfortably into a hydrophobic pocket formed by W34, Y39 and W46, the linking pyrazole hydrogen bonds to S36, and the nitro group may be involved in an electrostatic interaction with R96. Pyrazolone moieties exhibit pKa values of around 7 and therefore are >50% ionized at physiological pH. This physiochemical property accounts for their observed interactions with the cationic $Zn^{2+}$ ions in the active sites. Since this salt bridge interaction likely significantly contributes to the overall stability of the FosA-ANY1 complex, it can initially be retained. To garner greater hydrophobic interactions with the W34/Y39/W46 sub-pocket, the bromine atoms can be substituted with other hydrophobic moieties, including Cl, phenyl and alkyl groups. The nitro group can be omitted, i.e. compound 7 can be prepared, to determine its significance, and then putative bioisosteres of the nitro group, such as a carboxylic acid, $—SO_2CF_3$ can be introduced. The linking pyrazole can be varied with several other heterocycles that can still engage in the hydrogen bond with S36, such as imidazole and thiazole. In addition, the pyrazole ring can be broken open to afford a more flexible linker, such as $—CONHCH_2CH_2NHCO—$ to determine if a rigid linking unit is required.

Example 6

Treatment with Inhibitors of Fosfomycin-Modifying Enzymes

A subject having a condition that may be ameliorated with an embodiment of the disclosed compounds is identified and selected for treatment. The subject may have, for example, an infection mediated by a bacterium, such as a Gram-negative bacterium. In some cases, the bacterium is fosfomycin-resistant. The subject may be selected based on a clinical presentation and/or by performing tests to demonstrate presence of the infection. In some instances, a biological sample (e.g., urine or blood) from the subject is tested to determine whether the infection is caused by a fosfomycin-resistant bacterium.

The subject is treated by administering (i) fosfomycin or a pharmaceutically acceptable salt thereof, and (ii) a compound according to Formula A or Formula I as disclosed herein or a pharmaceutically acceptable salt thereof at amounts determined by a clinician to be therapeutically effective. The fosfomycin and compound are administered simultaneously or sequentially in any order. The fosfomycin and compound may be administered in separate pharmaceutical compositions or in a pharmaceutical composition comprising both components. The fosfomycin and compound are administered by any suitable means including, but not limited to, orally, parenterally, rectally, nasally, buccally, vaginally, topically, optically, by inhalation spray, or via an implanted reservoir.

A therapeutically effective amount of a third agent may be co-administered with the fosfomycin and the compound. The third agent may be administered either separately or together in a pharmaceutical composition with the fosfomycin, the compound, or both the fosfomycin and the compound. The third agent may be administered by the same route or a different route. If administered concurrently, the fosfomycin, the compound, and the third agent may be combined in a single pharmaceutical composition or may be administered concurrently as two or three pharmaceutical compositions. The third agent may be, for example, an antibiotic, a fever reducer, an anti-inflammatory agent, or any other active agent suitable for ameliorating one or more signs or symptoms of the infection.

Certain representative embodiments are disclosed in the following numbered clauses.

1. A pharmaceutical composition, comprising: fosfomycin or a pharmaceutically acceptable salt thereof; and a compound according to Formula A, or a stereoisomer, tautomer, or pharmaceutically acceptable salt thereof Formula A

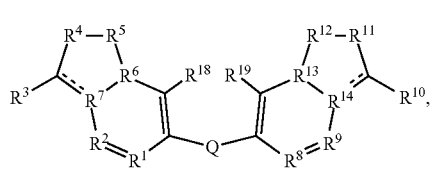

wherein (i) each bond indicated with " = " is a single bond or a double bond as needed to satisfy valency requirements, (ii) $R^1$, $R^2$, $R^8$, and $R^9$ independently are N, CH, C(OH), C(SH), C(CH$_3$), C(CFH$_2$), C(CF$_2$H), or C(CF$_3$), (iii) $R^3$ and $R^{10}$ independently are Br, F, Cl, OH, SH, NH$_2$, NO$_2$, alkyl, haloalkyl, or aryl, (iv) $R^4$ and $R^{11}$ independently are C=O, C=S, C(H)CH$_3$, C(H)CFH$_2$, C(H)CF$_2$H, C(H)CF$_3$, SO$_2$, SO, COOR' where R' is H or C$_1$-C$_5$ alkyl, or COO$^-$, (v) $R^5$ and $R^{12}$ independently are NR' where R' is H or C$_1$-C$_5$ alkyl, O, S, CH$_2$, C(H)OH, C(H)SH, C(H)CH$_3$, C(H)CFH$_2$, C(H)CF$_2$H, or C(H)CF$_3$, (vi) $R^6$ and $R^{13}$ independently are N or CH, (vii) $R^7$ and $R^{14}$ independently are N or C, (viii) $R^{18}$ and $R^{19}$ independently are H or C$_1$-C$_5$ alkyl, and (ix) Q is

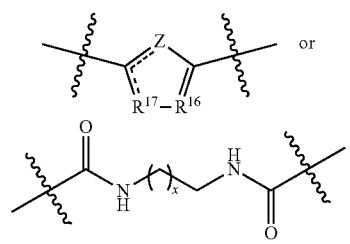

where x is 1, 2, 3, 4, or 5, each bond indicated with " = " is a single bond or a double bond as needed to satisfy valency requirements, Z is CR$^{15}$, S, N, or O, where R$^{15}$ is H, NO$_2$, COO$^-$, COOR', CN, CS$_2$, CH$_3$, CFH$_2$, CF$_2$H, CF$_3$, or SO$_2$CF$_3$, where R' is H or C$_1$-C$_5$ alkyl, $R^{16}$ is N, CH, C(OH), C(SH), C(CH$_3$), C(CFH$_2$), C(CF$_2$H), or C(CF$_3$), and $R^{17}$ is NH, N(CH$_3$), N, O, S, CH, CH$_2$, C(H)OH, C(H)SH, C(H)CH$_3$, C(H)CFH$_2$, C(H)CF$_2$H, or C(H)CF$_3$.

2. The pharmaceutical composition of clause 1, wherein Q is

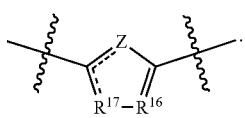

3. The pharmaceutical composition of clause 1, wherein Q is

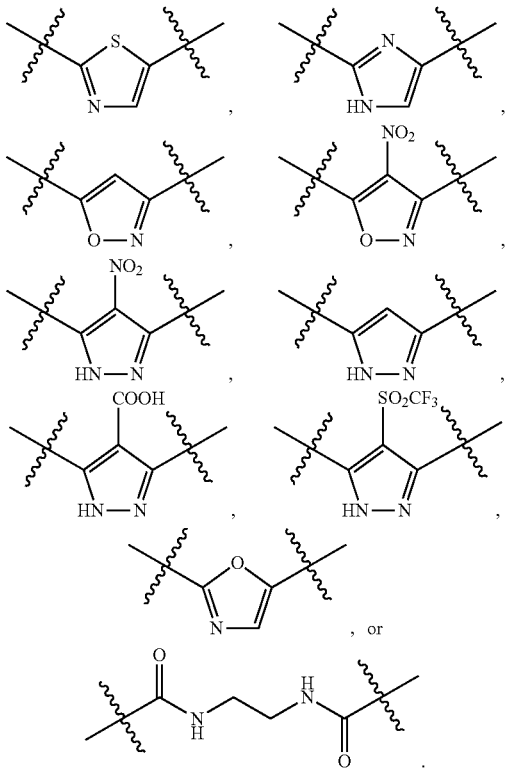

, or

4. The pharmaceutical composition of any one of clauses 1-3, wherein: (i) $R^1$ and $R^8$ are CH; (ii) $R^2$, $R^6$, $R^9$, and $R^{13}$ are N; (iii) $R^3$ and $R^{10}$ independently are Br, Cl, C$_1$-C$_5$ alkyl, phenyl, F, OH, SH, NH$_2$, NO$_2$, CFH$_2$, CF$_2$H, or CF$_3$; (iv) $R^4$ and $R^{11}$ are C(O); (v) $R^5$ and $R^{12}$ are NH; (vi) $R^6$ and $R^{13}$ are N; (vii) $R^7$ and $R^{14}$ are C; (viii) $R^{18}$ and $R^{19}$ are CH$_3$ or H; or (ix) any combination of (i), (ii), (iii), (iv), (v), (vi), (vii), and (viii).

5. A pharmaceutical composition, comprising: fosfomycin or a pharmaceutically acceptable salt thereof; and a compound according to Formula I, or a stereoisomer, tautomer, or pharmaceutically acceptable salt thereof Formula I

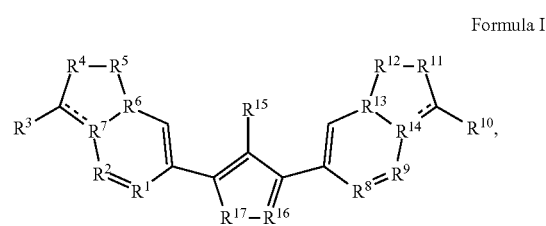

wherein (i) each bond indicated with " = " is a single bond or a double bond as needed to satisfy valency requirements, (ii) $R^1$, $R^2$, $R^8$, $R^9$ and $R^{16}$ independently are N, CH, C(OH), C(SH), C(CFH$_2$), C(CF$_2$H), or C(CF$_3$), (iii) $R^3$ and $R^{10}$ independently are Br, F, Cl, OH, SH, NH$_2$, NO$_2$, CH$_3$, CFH$_2$, CF$_2$H, or CF$_3$, (iv) $R^4$ and $R^{11}$ independently are C=O, C=S, C(H)CFH$_2$, C(H)CF$_2$H, C(H)CF$_3$, SO$_2$, or SO, (v) $R^5$, $R^{12}$, and $R^{17}$ independently are NH, NCH$_3$, O, S, CH$_2$, C(H)OH, C(H)SH, C(H)CFH$_2$, C(H)CF$_2$H, or C(H)CF$_3$, (vi) R$^6$ and R$^{13}$ independently are N or CH, (vii) R$^7$ and R$^{14}$ independently are N or C, and (viii) R$^{15}$ is NO$_2$, COO, CN, CS$_2$, CFH$_2$, CF$_2$H, or CF$_3$.

6. The pharmaceutical composition of clause 5, wherein: R$^1$ and R$^8$ are CH; R$^7$ and R$^{14}$ are C; and R$^2$, R$^6$, R$^9$, and R$^{13}$ are N.

7. The pharmaceutical composition of clause 5 or clause 6, wherein R$^3$ and R$^{10}$ are Br.

8. The pharmaceutical composition of any one of clauses 5-7, wherein R$^4$ and R$^{11}$ are C=O.

9. The pharmaceutical composition of any one of clauses 5-8 where R$^5$ and R$^{12}$ are NH.

10. The pharmaceutical composition of any one of clauses 5-9, wherein R$^{16}$ is N and R$^{17}$ is NH.

11. The pharmaceutical composition of any one of clauses 5-10, wherein R$^{15}$ is NO$_2$.

12. The pharmaceutical composition of clause 1, wherein the compound is

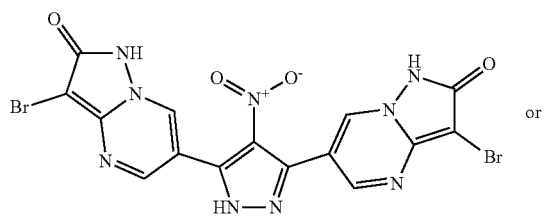

or

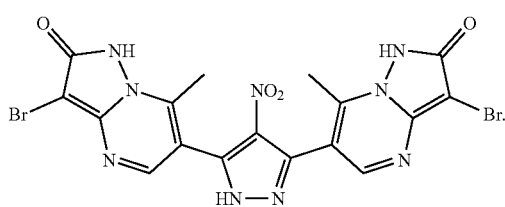

13. The pharmaceutical composition of clause 5, wherein the compound is

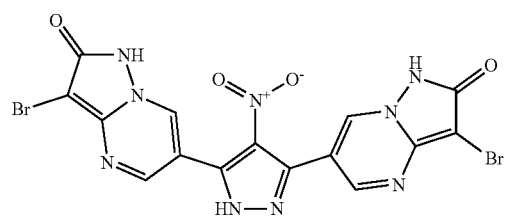 [SMILES: O=c1[nH]n2cc(-c3n[nH]c(-c4cnc5c(Br)c(=O)[nH]n5c4)c3[N+](=O)[O-])cnc2c1Br]

3-bromo-6-[3-(3-bromo-2-oxo-1H-pyrazolo[1,5-a]pyrimidin-6-yl)-4-nitro-1H-pyrazol-5-yl]1H-pyrazolo[1,5-a]pyrimidin-2-one.

14. The pharmaceutical composition of any one of clauses 1-3, further comprising a pharmaceutically acceptable carrier.

15. A compound according to Formula A, or a stereoisomer, tautomer, or pharmaceutically acceptable salt thereof

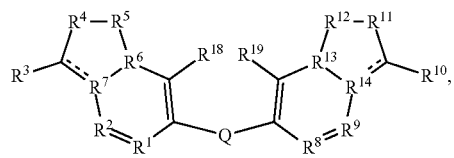

Formula A wherein each bond indicated with "═" is a single bond or a double bond as needed to satisfy valency requirements; R$^1$, R$^2$, R$^8$, and R$^9$ independently are N, CH, C(OH), C(SH), C(CH$_3$), C(CFH$_2$), C(CF$_2$H), or C(CF$_3$); R$^3$ and R$^{10}$ independently are Br, F, Cl, OH, SH, NH$_2$, NO$_2$, alkyl, haloalkyl, or aryl; R$^4$ and R$^{11}$ independently are C=O, C=S, C(H)CH$_3$, C(H)CFH$_2$, C(H)CF$_2$H, C(H)CF$_3$, SO$_2$, SO, COOR' where R' is H or C$_1$-C$_5$ alkyl, or COO$^-$; R$^5$ and R$^{12}$ independently are NR' where R' is H or C$_1$-C$_5$ alkyl, O, S, CH$_2$, C(H)OH, C(H)SH, C(H)CH$_3$, C(H)CFH$_2$, C(H)CF$_2$H, or C(H)CF$_3$; R$^6$ and R$^{13}$ independently are N or CH; R$^7$ and R$^{14}$ independently are N or C; and Q is

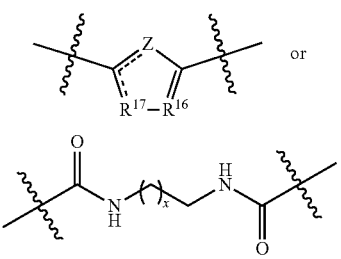

or where x is 1, 2, 3, 4, or 5, each bond indicated with "═" is a single bond or a double bond as needed to satisfy valency requirements, Z is CR$^{15}$, S, N, or O, where R$^{15}$ is H, NO$_2$, COO$^-$, COOR', CN, CS$_2$, CH$_3$, CFH$_2$, CF$_2$H, CF$_3$, or SO$_2$CF$_3$, where R' is H or C$_1$-C$_5$ alkyl, R$^{16}$ is N, CH, C(OH), C(SH), C(CH$_3$), C(CFH$_2$), C(CF$_2$H), or C(CF$_3$), and R$^{17}$ is NH, N(CH$_3$), N, O, S, CH, CH$_2$, C(H)OH, C(H)SH, C(H)CH$_3$, C(H)CFH$_2$, C(H)CF$_2$H, or C(H)CF$_3$, wherein the compound is not:

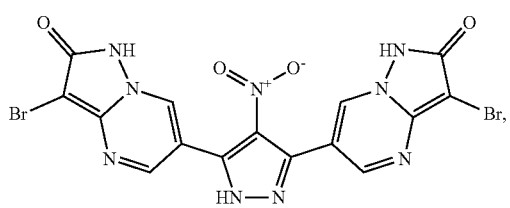

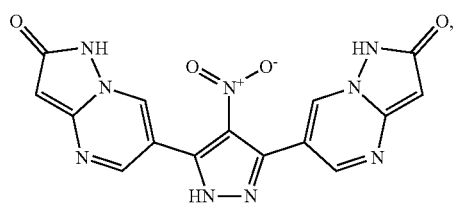

35

-continued

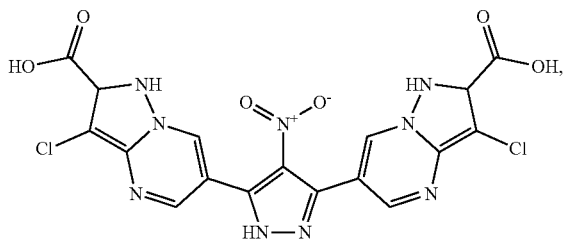

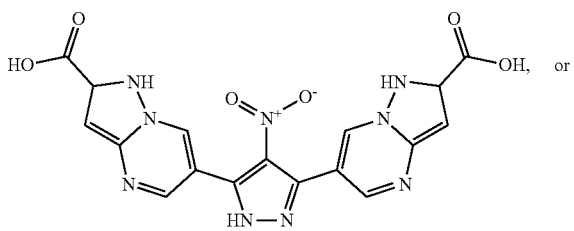

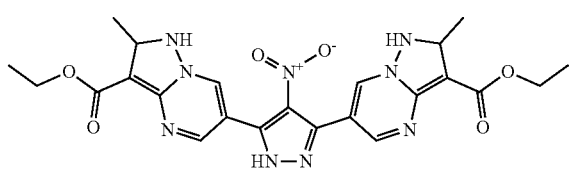 or

16. The compound of clause 15, wherein Q is

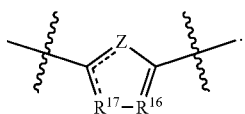

17. The compound of clause 15, wherein Q is

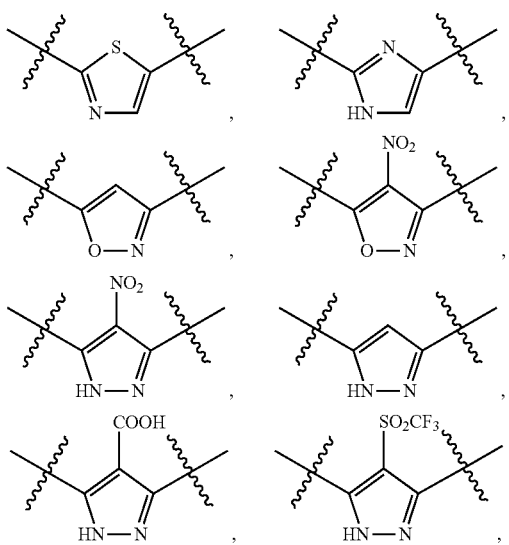

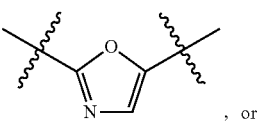, or

36

-continued

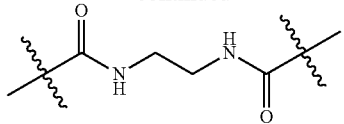.

18. The compound of any one of clauses 15-17, wherein: (i) $R^1$ and $R^8$ are CH; (ii) $R^2$, $R^6$, $R^9$, and $R^{13}$ are N; (iii) $R^3$ and $R^{10}$ independently are Br, Cl, $C_1$-$C_5$ alkyl, phenyl, F, OH, SH, $NH_2$, $NO_2$, $CFH_2$, $CF_2H$, or $CF_3$; (iv) $R^4$ and $R^{11}$ are C(O); (v) $R^5$ and $R^{12}$ are NH; (vi) $R^6$ and $R^{13}$ are N; (vii) $R^7$ and $R^{14}$ are C; (viii) $R^{18}$ and $R^{19}$ are $CH_3$; or (ix) any combination of (i), (ii), (iii), (iv), (v), (vi), (vii), and (viii).

19. The compound of clause 15, wherein the compound is

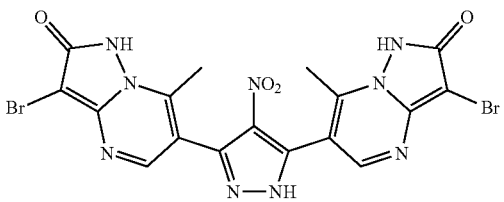 [SMILES: Cc1c(-c2n[nH]c(-c3cnc4c(Br)c(=O)[nH]n4c3C)c2[N+](=O)[O-])cnc2c(Br)c(=O)[nH]n12]

6,6'-(4-nitro-1H-pyrazole-3,5-diyl)bis(3-bromo-7-methylpyrazolo[1,5-a]pyrimidin-2(1H)-one).

20. A method of inhibiting growth of a fosfomycin-resistant bacterium, comprising: contacting a fosfomycin-resistant bacterium with (i) fosfomycin or a pharmaceutically acceptable salt thereof and (ii) an effective amount of a compound according to Formula A, or a stereoisomer, tautomer, or pharmaceutically acceptable salt thereof

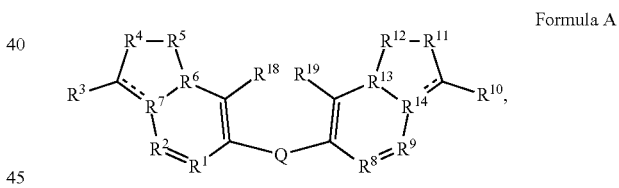

Formula A wherein each bond indicated with " === " is a single bond or a double bond as needed to satisfy valency requirements, $R^1$, $R^2$, $R^8$, and $R^9$ independently are N, CH, C(OH), C(SH), C(CFH$_2$), C(CF$_2$H), or C(CF$_3$), $R^3$ and $R^{10}$ independently are Br, F, Cl, OH, SH, NH$_2$, NO$_2$, alkyl, haloalkyl, or aryl, $R^4$ and $R^{11}$ independently are C=O, C=S, C(H)CFH$_2$, C(H)CF$_2$H, C(H)CF$_3$, SO$_2$, SO, COOR' where R' is H or $C_1$-$C_5$ alkyl, or COO$^-$, $R^5$ and $R^{12}$ independently are NR' where R' is H or $C_1$-$C_5$ alkyl, O, S, CH$_2$, C(H)OH, C(H)SH, C(H)CH$_3$, C(H)CFH$_2$, C(H)CF$_2$H, or C(H)CF$_3$, $R^6$ and $R^{13}$ independently are N or CH, $R^7$ and $R^{14}$ independently are N or C, $R^{18}$ and $R^{19}$ independently are H or $C_1$-$C_5$ alkyl, and Q is

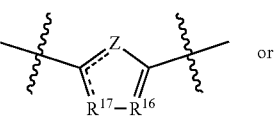 or

-continued

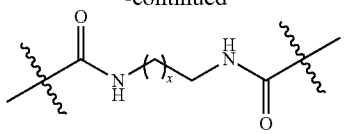

where x is 1, 2, 3, 4, or 5, each bond indicated with " =  " is a single bond or a double bond as needed to satisfy valency requirements, Z is $CR^{15}$, S, N, or O, where $R^{15}$ is H, $NO_2$, $COO^-$, COOR', CN, $CS_2$, $CH_3$, $CFH_2$, $CF_2H$, $CF_3$, or $SO_2CF_3$, where R' is H or $C_1$-$C_5$ alkyl, $R^{16}$ is N, CH, C(OH), C(SH), $C(CFH_2)$, $C(CF_2H)$, or $C(CF_3)$, and $R^{17}$ is NH, $N(CH_3)$, N, O, S, CH, $CH_2$, C(H)OH, C(H)SH, $C(H)CH_3$, $C(H)CFH_2$, $C(H)CF_2H$, or $C(H)CF_3$.

21. The method of clause 20, wherein: (i) $R^1$ and $R^8$ are CH; (ii) $R^7$ and $R^{14}$ are C; (iii) $R^2$, $R^6$, $R^9$, and $R^{13}$ are N; (iv) $R^3$ and $R^{10}$ are Br; (v) $R^4$ and $R^{11}$ are C=O, (vi) $R^5$ and $R^{12}$ are NH; (vii) $R^{16}$ is N and $R^{17}$ is NH; (viii) $R^{15}$ is $NO_2$; or (ix) any combination of (i), (ii), (iii), (iv), (v), (vi), (vii), and (viii).

22. The method of clause 20 or clause 21, wherein Q is

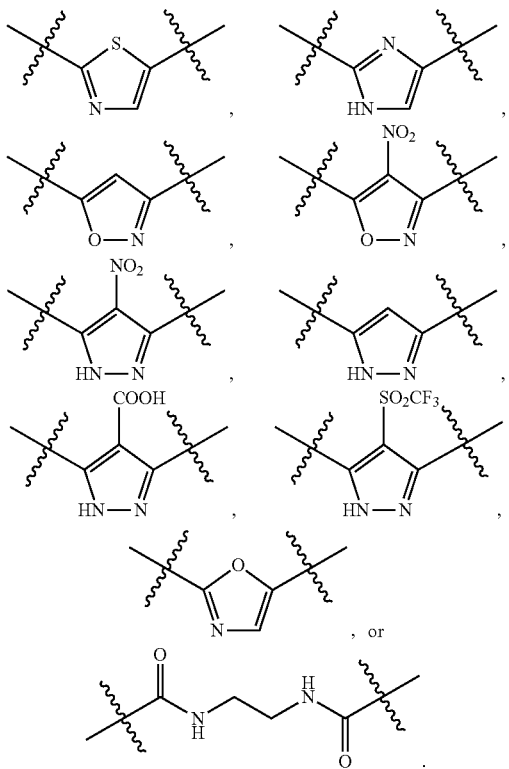

, or

23. The method of clause 20, wherein the compound is

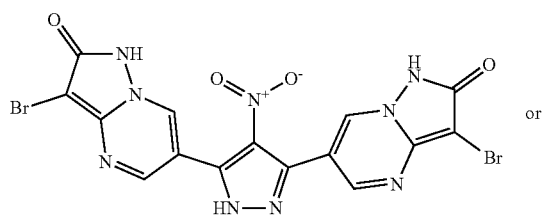

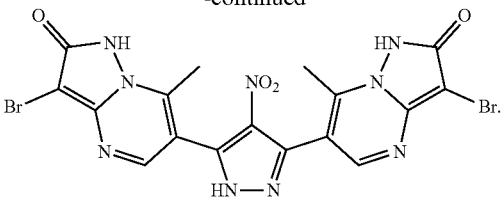

24. The method of any one of clauses 20-23, where the fosfomycin-resistant bacterium is a bacterium that produces a FosA enzyme.

25. The method of any one of clauses 20-24, where the fosfomycin-resistant bacterium is a Gram-negative bacterium.

26. The method of any one of clauses 20-25, wherein the effective amount of the compound is within a range of 5 μM to 20 μM.

27. The method of any one of clauses 20-26, wherein contacting the fosfomycin-resistant bacterium comprises administering a therapeutically effective amount of fosfomycin or pharmaceutically acceptable salt thereof and the effective amount of the compound or pharmaceutically acceptable salt thereof to a subject identified as having, or being at risk of having, an infection caused by a fosfomycin-resistant bacterium.

28. The method of clause 27, wherein administering the therapeutically effective amount of fosfomycin or pharmaceutically acceptable salt thereof and the effective amount of the compound or pharmaceutically acceptable salt thereof is performed simultaneously or sequentially in any order.

29. The method of clause 27, wherein administering the therapeutically effective amount of fosfomycin or pharmaceutically acceptable salt thereof and the effective amount of Formula I or pharmaceutically acceptable salt thereof comprises administering an amount of a pharmaceutical composition comprising the therapeutically effective amount of fosfomycin or pharmaceutically acceptable salt thereof and the effective amount of the compound or pharmaceutically acceptable salt thereof.

30. The method of any one of clauses 27-29, wherein the compound is

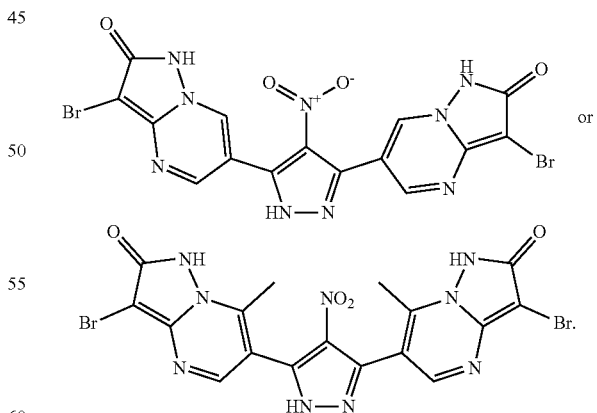

31. A method of inhibiting growth of a fosfomycin-resistant bacterium, comprising: contacting a fosfomycin-resistant bacterium with (i) fosfomycin or a pharmaceutically acceptable salt thereof and (ii) an effective amount of a compound according to Formula I or a pharmaceutically acceptable salt thereof

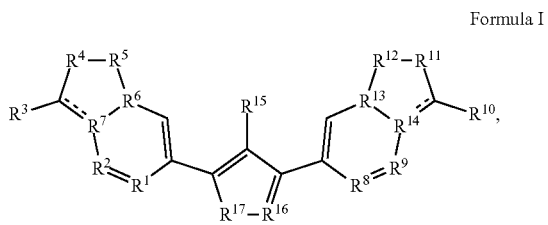

Formula I wherein bonds indicated with "===" are single bonds or double bonds as needed to satisfy valency requirements, $R^1$, $R^2$, $R^8$, $R^9$ and $R^{16}$ independently are N, CH, C(OH), C(SH), C(CFH$_2$), C(CF$_2$H), or C(CF$_3$), $R^3$ and $R^{10}$ independently are Br, F, Cl, OH, SH, NH$_2$, NO$_2$, CH$_3$, CFH$_2$, CF$_2$H, or CF$_3$, $R^4$ and $R^{11}$ independently are C=O, C=S, C(H)CFH$_2$, C(H)CF$_2$H, C(H)CF$_3$, SO$_2$, or SO, $R^5$, $R^{12}$, and $R^{17}$ independently are NH, NCH$_3$, O, S, CH$_2$, C(H)OH, C(H)SH, C(H)CFH$_2$, C(H)CF$_2$H, or C(H)CF$_3$, $R^6$ and $R^{13}$ independently are N or CH, $R^7$ and $R^{14}$ independently are N or C; and $R^{15}$ is NO$_2$, COO$^-$, CN, CS$_2$, CFH$_2$, CF$_2$H, or CF$_3$.

32. The method of clause 31, wherein $R^1$ and $R^8$ are CH; $R^7$ and $R^{14}$ are C; and $R^2$, $R^6$, $R^9$, and $R^{13}$ are N.

33. The method of clause 31 or clause 32, wherein $R^3$ and $R^{10}$ are Br.

34. The method of any one of clauses 31-33, wherein $R^4$ and $R^{11}$ are C=O.

35. The method of any one of clauses 31-34, wherein $R^5$ and $R^{12}$ are NH.

36. The method of any one of clauses 31-35, wherein $R^{16}$ is N and $R^{17}$ is NH.

37. The method of any one of clauses 31-36, wherein $R^{15}$ is NO$_2$.

38. The method of any one of clauses 31-37, wherein the fosfomycin-resistant bacterium is a bacterium that produces a FosA enzyme.

39. The method of any one of clauses 31-38, where the fosfomycin-resistant bacterium is a Gram-negative bacterium.

40. The method of any one of clauses 31-39, wherein the effective amount of the compound is within a range of 5 μM to 20 μM.

41. The method of any one of clauses 31-40, wherein contacting the fosfomycin-resistant bacterium comprises administering a therapeutically effective amount of fosfomycin or pharmaceutically acceptable salt thereof and the effective amount of the compound or pharmaceutically acceptable salt thereof to a subject identified as having, or being at risk of having, an infection caused by a fosfomycin-resistant bacterium.

42. The method of clause 41, wherein administering the therapeutically effective amount of fosfomycin or pharmaceutically acceptable salt thereof and the effective amount of the compound or pharmaceutically acceptable salt thereof is performed simultaneously or sequentially in any order.

43. The method of clause 41, wherein administering the therapeutically effective amount of fosfomycin or pharmaceutically acceptable salt thereof and the effective amount of Formula I or pharmaceutically acceptable salt thereof comprises administering an amount of a pharmaceutical composition comprising the therapeutically effective amount of fosfomycin or pharmaceutically acceptable salt thereof and the effective amount of the compound or pharmaceutically acceptable salt thereof.

44. The method of any one of clauses 41-43, wherein the compound is

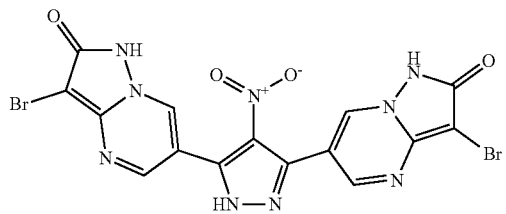 [SMILES: O=c1[nH]n2cc(-c3n[nH]c(-c4cnc5c(Br)c(=O)[nH]n5c4)c3[N+](=O)[O-])cnc2c1Br]

3-bromo-6-[3(3-bromo-2-oxo-1H-pyrazolo[1,5-a]pyrimidin-6-yl)-4-nitro-1H-pyrazol-5-yl]-1H-pyrazolo[1,5-a]pyrimidin-2-one, and the effective amount is an amount sufficient to provide an in vivo concentration within a range of 5 μM to 20 μM.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A pharmaceutical composition, comprising:
   fosfomycin or a pharmaceutically acceptable salt thereof; and
   a compound according to Formula A, or a stereoisomer, tautomer, or pharmaceutically acceptable salt thereof

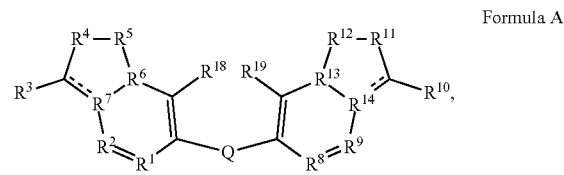

Formula A wherein
  each bond indicated with "===" is a single bond or a double bond as needed to satisfy valency requirements,
  $R^1$ and $R^8$ are CH,
  $R^3$ and $R^{10}$ independently are Br, F, Cl, OH, SH, NH$_2$, NO$_2$, alkyl, haloalkyl, or aryl,
  $R^4$ and $R^{11}$ are C=O,
  $R^5$ and $R^{12}$ are NH,
  $R^2$, $R^6$, $R^9$ and $R^{13}$ are N,
  $R^7$ and $R^{14}$ are C,
  $R^{18}$ and $R^{19}$ independently are H or $C_1$-$C_5$ alkyl, and
  Q is

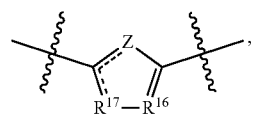

where
  each bond indicated with "===" is a single bond or a double bond as needed to satisfy valency requirements,
  Z is CR$^{15}$, where R$^{15}$ is H, NO$_2$, COO$^-$, COOR', CN, CH$_3$, CFH$_2$, CF$_2$H, CF$_3$, or SO$_2$CF$_3$, where R' is H or $C_1$-$C_5$ alkyl,
  R$^{16}$ is N, and
  R$^{17}$ is NH.

2. The pharmaceutical composition of claim 1, wherein Q is

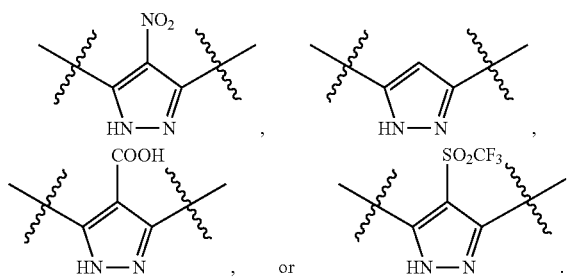

3. The pharmaceutical composition of claim 1, wherein:
(i) $R^3$ and $R^{10}$ independently are Br, Cl, $C_1$-$C_5$ alkyl, phenyl, F, OH, SH, $NH_2$, $NO_2$, $CFH_2$, $CF_2H$, or $CF_3$;
(ii) $R^{18}$ and $R^{19}$ are $CH_3$ or H; or
(iii) both (i) and (ii).

4. The pharmaceutical composition of claim 1, wherein the compound has a structure according to Formula I, or a stereoisomer, tautomer, or pharmaceutically acceptable salt thereof Formula I

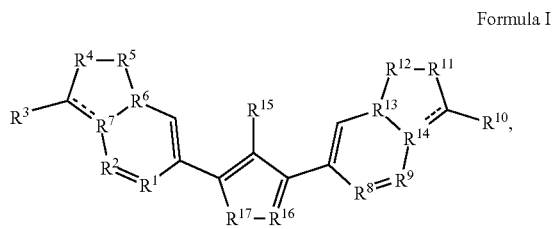

wherein
each bond indicated with " ═ " is a single bond or a double bond as needed to satisfy valency requirements,
$R^1$, and $R^8$ are CH,
$R^3$ and $R^{10}$ independently are Br, F, Cl, OH, SH, $NH_2$, $NO_2$, $CH_3$, $CFH_2$, $CF_2H$, or $CF_3$,
$R^4$ and $R^{11}$ are C═O,
$R^5$, $R^{12}$, and $R^{17}$ are NH,
$R^2$, $R^6$, $R^9$, $R^{13}$, and $R^{16}$ are N,
$R^7$ and $R^{14}$ are C, and
$R^{15}$ is $NO_2$, $COO^-$, CN, $CFH_2$, $CF_2H$, or $CF_3$.

5. The pharmaceutical composition of claim 4, wherein:
(i) $R^3$ and $R^{10}$ are Br; or
(ii) $R^{15}$ is $NO_2$; or
(iii) both (i) and (ii).

6. A pharmaceutical composition comprising:
fosfomycin or a pharmaceutically acceptable salt thereof; and
a compound, wherein the compound is

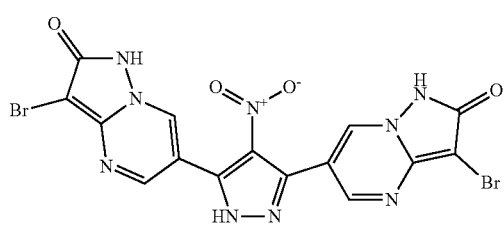 [SMILES: O=c1[nH]n2cc(-c3n[nH]c(-c4cnc5c(Br)c(=O)[nH]n5c4)c3[N+](=O)[O-])cnc2c1Br]

3-bronco-6-[3-(3-bromo-2-oxo-1H-pyrazolo[1,5-a]pyrimidin-6-yl)-4-1H-pyrazolo-5-yl]-1H-pyrazolo[1,5-a]pyrimidin-2-one
or

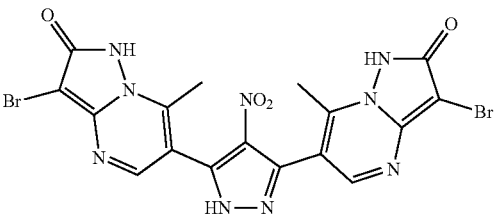 [SMILES: Cc1c(-c2n[nH]c(-c3cnc4c(Br)c(=O)[nH]n4c3C)c2[N+](=O)[O-])cnc2c(Br)c(=O)[nH]n12]

6,6'-(4-nitro-1H-pyrazole-3,5-diyl)bis(3-bromo-7-methylpyrazolo[1,5-a]pyrimidin-2(1H)-one).

7. A method of inhibiting growth of a fosfomycin-resistant bacterium, comprising:
contacting a fosfomycin-resistant bacterium with a pharmaceutical composition according to claim 1.

8. The method of claim 7, wherein the compound has a structure according to Formula I or a pharmaceutically acceptable salt thereof Formula I

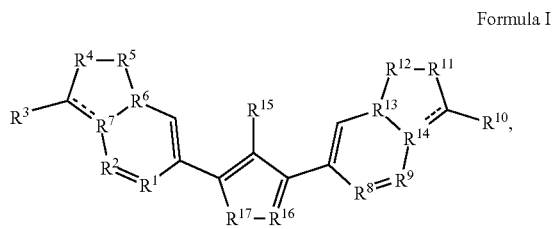

wherein
bonds indicated with " ═ " are single bonds or double bonds as needed to satisfy valency requirements,
$R^1$, and $R^8$ are CH,
$R^3$ and $R^{10}$ independently are Br, F, Cl, OH, SH, $NH_2$, $NO_2$, $CH_3$, $CFH_2$, $CF_2H$, or $CF_3$,
$R^4$ and $R^{11}$ are C═O,
$R^5$, $R^{12}$, and $R^{17}$ are NH,
$R^2$, $R^6$, $R^9$, $R^{13}$, and $R^{16}$ are N,
$R^7$ and $R^{14}$ are C, and
$R^{15}$ is $NO_2$, $COO^-$, CN, $CFH_2$, $CF_2H$, or $CF_3$.

9. The method of claim 7, wherein:
(i) $R^3$ and $R^{10}$ are Br; or
(ii) $R^{15}$ is $NO_2$; or
(iii) both (i) and (ii).

10. The method of claim 7, wherein:
(i) the fosfomycin-resistant bacterium is a bacterium that produces a FosA enzyme; or
(ii) the fosfomycin-resistant bacterium is a Gram-negative bacterium; or
(iii) both (i) and (ii).

11. The method of claim 7, wherein the effective amount of the compound is within a range of 5 μM to 20 μM.

12. The method of claim 7, wherein contacting the fosfomycin-resistant bacterium comprises administering a therapeutically effective amount of fosfomycin or pharmaceutically acceptable salt thereof and the effective amount of the compound or pharmaceutically acceptable salt thereof to a subject identified as having an infection caused by a fosfomycin-resistant bacterium.

13. The method of claim 12, wherein:

administering the therapeutically effective amount of fosfomycin or pharmaceutically acceptable salt thereof and the effective amount of the compound or pharmaceutically acceptable salt thereof is performed simultaneously or sequentially in any order; or administering the therapeutically effective amount of fosfomycin or pharmaceutically acceptable salt thereof and the effective amount of Formula I or pharmaceutically acceptable salt thereof comprises administering an amount of a pharmaceutical composition comprising the therapeutically effective amount of fosfomycin or pharmaceutically acceptable salt thereof and the effective amount of the compound or pharmaceutically acceptable salt thereof.

14. The method of claim 12, wherein the compound is

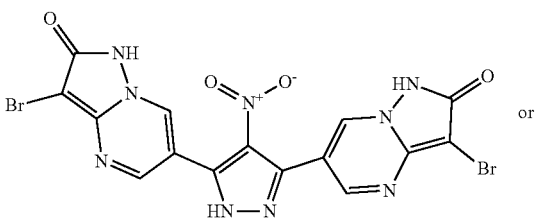 or

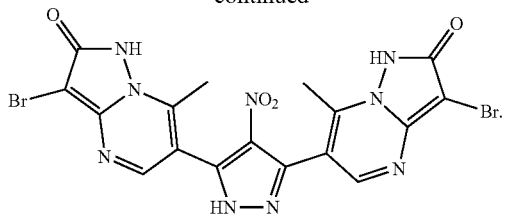

15. The method of claim 12, wherein the compound is

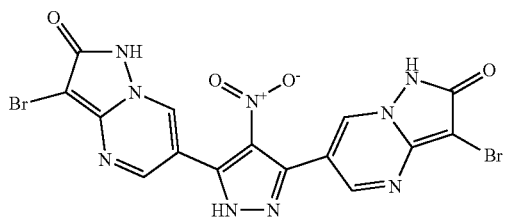 [SMILES: O=c1[nH]n2cc(-c3n[nH]c(-c4cnc5c(Br)c(=O)[nH]n5c4)c3[N+](=O)[O-])cnc2c1Br]

3-bromo-6-[3-(3-bromo-2-oxo-1H-pyrazolo[1,5-a[pyrimidin-6-yl)-4-nitro-1H-pyrazol-5-yl]-1H-pyrazolo[1,5-a]pyrimidin-2-one, and
the effective amount is an amount sufficient to provide an in vivo concentration within a range of 5 µM to 20 µM.

16. A method of inhibiting growth of a fosfomycin-resistant bacterium, comprising:
contacting a fosfomycin-resistant bacterium with a pharmaceutical composition according to claim 8.

* * * * *